(12) United States Patent
Yocum et al.

(10) Patent No.: US 7,244,593 B2
(45) Date of Patent: Jul. 17, 2007

(54) MICROORGANISMS AND PROCESSES FOR ENHANCED PRODUCTION OF PANTOTHENATE

(75) Inventors: R. Roger Yocum, Lexington, MA (US); Thomas A. Patterson, North Attleboro, MA (US); Janice G. Pero, Lexington, MA (US); Theron Hermann, Kinnelon, NJ (US)

(73) Assignee: BASF Aktiengesellschaft (DE)

( * ) Notice: Subject to any disclaimer, the term of this patent is extended or adjusted under 35 U.S.C. 154(b) by 323 days.

(21) Appl. No.: 10/466,641

(22) PCT Filed: Jan. 18, 2002

(86) PCT No.: PCT/US02/00925

§ 371 (c)(1),
(2), (4) Date: Jul. 18, 2003

(87) PCT Pub. No.: WO02/061108

PCT Pub. Date: Aug. 8, 2002

(65) Prior Publication Data

US 2004/0091979 A1  May 13, 2004

Related U.S. Application Data

(60) Provisional application No. 60/347,638, filed on Jan. 11, 2002, provisional application No. 60/263,053, filed on Jan. 19, 2001, provisional application No. 60/262,995, filed on Jan. 19, 2001.

(51) Int. Cl.
    *C12P 13/04* (2006.01)

(52) U.S. Cl. ............. 435/106; 435/183; 435/189; 435/193; 435/232; 435/252.3

(58) Field of Classification Search ............ 435/128, 435/252.3, 320.1, 106, 183, 189, 193, 232; 536/23.2

See application file for complete search history.

(56) References Cited

U.S. PATENT DOCUMENTS

| | | | |
|---|---|---|---|
| 6,184,006 B1 * | 2/2001 | Rieping et al. | 435/128 |
| 6,184,007 B1 * | 2/2001 | Dusch et al. | 435/128 |
| 6,787,334 B1 * | 9/2004 | Elischweski et al. | 435/69.1 |

OTHER PUBLICATIONS

Sigma product Nos. are P2250, P3161 & P9153.*

* cited by examiner

*Primary Examiner*—Tekchand Saidha
(74) *Attorney, Agent, or Firm*—Lahive & Cockfield, LLP; Elizabeth A. Hanley, Esq.; Debra J. Milasincic, Esq.

(57) ABSTRACT

The present invention features improved methods for the enhanced production of pantoate and pantothenate utilizing microorganisms having modified pantothenate biosynthetic enzyme activities and having modified methylenetetrahydrofolate (MTF) biosynthetic enzyme activities. In particular, the invention features methods for enhancing production of desired products by increasing levels of a key intermediate, ketopantoate by enzymes that contribute to its synthesis. Recombinant microorganisms and conditions for culturing same are also are featured. Also featured are compositions produced by such microorganisms.

34 Claims, 7 Drawing Sheets

FIG. 3
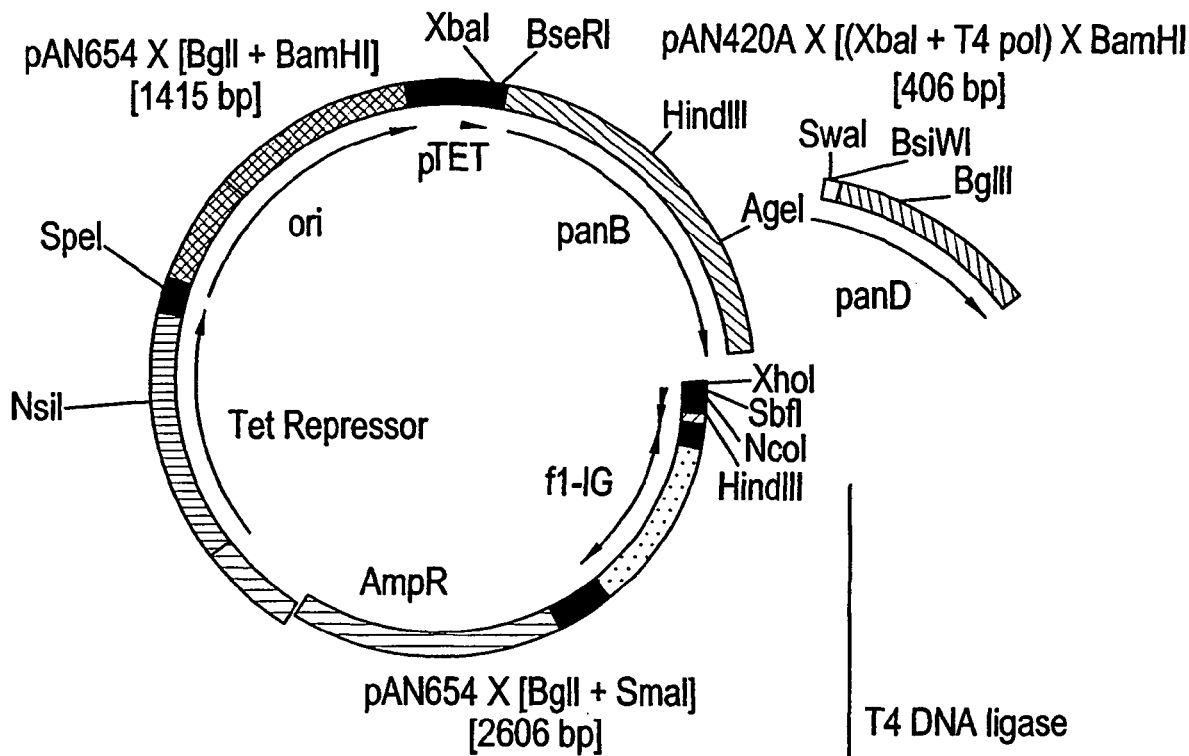
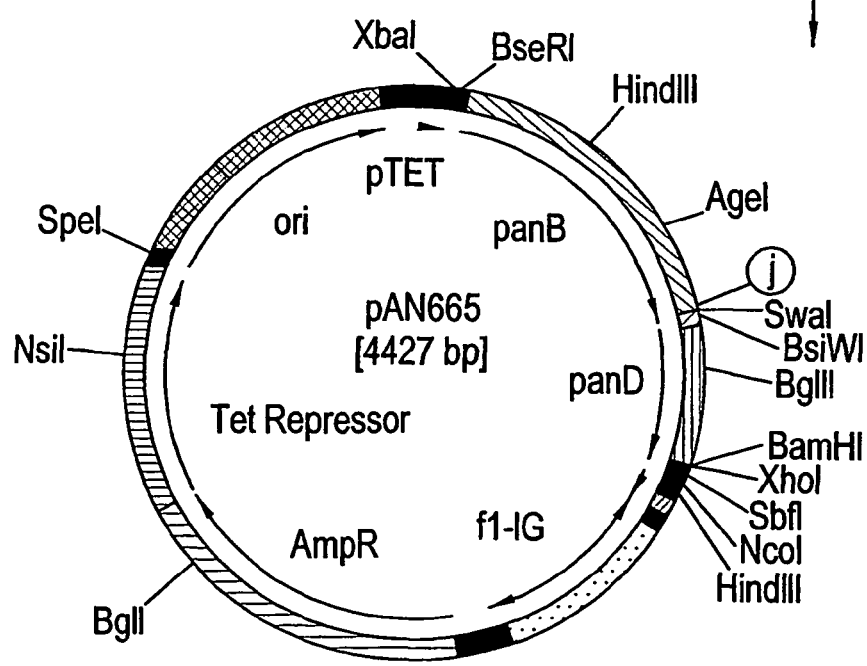

SEQUENCE LISTING

```
<160> NUMBER OF SEQ ID NOS: 25

<210> SEQ ID NO 1
<211> LENGTH: 194
<212> TYPE: DNA
<213> ORGANISM: Artificial Sequence
<220> FEATURE:
<223> OTHER INFORMATION: Description of Artificial Sequence:promoter
      sequence
<220> FEATURE:
<221> NAME/KEY: -35_signal
<222> LOCATION: (136)..(141)
<220> FEATURE:
<221> NAME/KEY: -10_signal
<222> LOCATION: (159)..(164)

<400> SEQUENCE: 1
gctattgacg acagctatgg ttcactgtcc accaaccaaa actgtgctca gtaccgccaa      60
tatttctccc ttgaggggta caaagagctg tccctagaag agatccacgc tgtgtaaaaa     120
ttttacaaaa aggtattgac tttccctaca gggtgtgtaa taatttaatt acaggcgggg     180
gcaaccccgc ctgt                                                      194
```

```
<210> SEQ ID NO 2
<211> LENGTH: 163
<212> TYPE: DNA
<213> ORGANISM: Artificial Sequence
<220> FEATURE:
<223> OTHER INFORMATION: Description of Artificial Sequence:promoter
      sequence
<220> FEATURE:
<221> NAME/KEY: -35_signal
<222> LOCATION: (113)..(118)
<220> FEATURE:
<221> NAME/KEY: -10_signal
<222> LOCATION: (136)..(141)

<400> SEQUENCE: 2
gcctacctag cttccaagaa agatatccta acagcacaag agcggaaaga tgttttgttc      60
tacatccaga acaacctctg ctaaaattcc tgaaaaattt tgcaaaaagt tgttgacttt    120
atctacaagg tgtggtataa taatcttaac aacagcagga cgc                      163

<210> SEQ ID NO 3
<211> LENGTH: 127
<212> TYPE: DNA
<213> ORGANISM: Artificial Sequence
<220> FEATURE:
<223> OTHER INFORMATION: Description of Artificial Sequence:promoter
      sequence
<220> FEATURE:
<221> NAME/KEY: -35_signal
<222> LOCATION: (34)..(39)
<220> FEATURE:
<221> NAME/KEY: -10_signal
<222> LOCATION: (58)..(63)
<220> FEATURE:
<221> NAME/KEY: -35_signal
<222> LOCATION: (75)..(80)
<220> FEATURE:
<221> NAME/KEY: -10_signal
<222> LOCATION: (98)..(103)

<400> SEQUENCE: 3
gaggaatcat agaattttgt caaaataatt ttattgacaa cgtcttatta acgttgatat      60
aatttaaatt ttatttgaca aaaatgggct cgtgttgtac aataaatgta gtgaggtgga    120
tgcaatg                                                              127

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence:ribosome
      binding site

<400> SEQUENCE: 4
taaacatgag gaggagaaaa catg                                            24

<210> SEQ ID NO 5
<211> LENGTH: 28
<212> TYPE: DNA
<213> ORGANISM: Artificial Sequence
<220> FEATURE:
<223> OTHER INFORMATION: Description of Artificial Sequence:ribosome
      binding site

<400> SEQUENCE: 5
attcgagaaa tggagagaat ataatatg                                        28

<210> SEQ ID NO 6
```

```
<211> LENGTH: 13
<212> TYPE: DNA
<213> ORGANISM: Artificial Sequence
<220> FEATURE:
<223> OTHER INFORMATION: Description of Artificial Sequence:ribosome
      binding site

<400> SEQUENCE: 6
agaaaggagg tga                                                          13

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence:ribosome
      binding site
<220> FEATURE:
<223> OTHER INFORMATION: All occurrences of n = any nucleotide

<400> SEQUENCE: 7
ttaagaaagg aggtgannnn atg                                               23

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence:ribosome
      binding site
<220> FEATURE:
<223> OTHER INFORMATION: All occurrences of n = any nucleotide

<400> SEQUENCE: 8
ttagaaagga ggtgannnnn atg                                               23

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence:ribosome
      binding site
<220> FEATURE:
<223> OTHER INFORMATION: All occurrences of n = any nucleotide

<400> SEQUENCE: 9
agaaaggagg tgannnnnnn atg                                               23

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence:ribosome
      binding site
<220> FEATURE:
<223> OTHER INFORMATION: All occurrences of n = any nucleotide

<400> SEQUENCE: 10
agaaaggagg tgannnnnna tg                                                22

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence:ribosome
      binding site
```

<400> SEQUENCE: 11
ccctctagaa ggaggagaaa acatg                                    25

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence:ribosome
      binding site

<400> SEQUENCE: 12
ccctctagag gaggagaaaa catg                                     24

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence:ribosome
      binding site

<400> SEQUENCE: 13
ttagaaagga ggatttaaat atg                                      23

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence:ribosome
      binding site

<400> SEQUENCE: 14
ttagaaagga ggtttaatta atg                                      23

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence:ribosome
      binding site

<400> SEQUENCE: 15
ttagaaagga ggtgatttaa atg                                      23

<210> SEQ ID NO 16
<211> LENGTH: 23
<212> TYPE: DNA
<213> ORGANISM: Artificial Sequence
<220> FEATURE:
<223> OTHER INFORMATION: Description of Artificial Sequence:ribosome
      binding site

<400> SEQUENCE: 16
ttagaaagga ggtgtttaaa atg                                      23

<210> SEQ ID NO 17
<211> LENGTH: 28
<212> TYPE: DNA
<213> ORGANISM: Artificial Sequence
<220> FEATURE:
<223> OTHER INFORMATION: Description of Artificial Sequence:ribosome
      binding site

```
<400> SEQUENCE: 17
attcgagaaa ggaggtgaat ataatatg                                         28

<210> SEQ ID NO 18
<211> LENGTH: 27
<212> TYPE: DNA
<213> ORGANISM: Artificial Sequence
<220> FEATURE:
<223> OTHER INFORMATION: Description of Artificial Sequence:ribosome
      binding site

<400> SEQUENCE: 18
attcgagaaa ggaggtgaat aataatg                                          27

<210> SEQ ID NO 19
<211> LENGTH: 28
<212> TYPE: DNA
<213> ORGANISM: Artificial Sequence
<220> FEATURE:
<223> OTHER INFORMATION: Description of Artificial Sequence:ribosome
      binding site

<400> SEQUENCE: 19
attcgtagaa aggaggtgaa ttaatatg                                         28

<210> SEQ ID NO 20
<211> LENGTH: 51
<212> TYPE: DNA
<213> ORGANISM: Artificial Sequence
<220> FEATURE:
<223> OTHER INFORMATION: 5' PCR primer for serA gene

<400> SEQUENCE: 20
ccctctagag gaggagaaaa catgtttcga gtattggtct cagacaaaat g               51

<210> SEQ ID NO 21
<211> LENGTH: 43
<212> TYPE: DNA
<213> ORGANISM: Artificial Sequence
<220> FEATURE:
<223> OTHER INFORMATION: 3' PCR primer for serA gene

<400> SEQUENCE: 21
cccggatcca attatggcag atcaatgagc ttcacagaca caa                        43

<210> SEQ ID NO 22
<211> LENGTH: 48
<212> TYPE: DNA
<213> ORGANISM: Artificial Sequence
<220> FEATURE:
<223> OTHER INFORMATION: 5' PCR primer for glyA gene

<400> SEQUENCE: 22
ggatctagag gaggtgtaaa catgaaacat ttacctgcgc aagacgaa                   48

<210> SEQ ID NO 23
<211> LENGTH: 43
<212> TYPE: DNA
<213> ORGANISM: Artificial Sequence
<220> FEATURE:
<223> OTHER INFORMATION: 3' PCR primer for glyA gene

<400> SEQUENCE: 23
cggggatccc ccatcaacaa ttacacactt ctattgattc tac                        43
```

-continued

<210> SEQ ID NO 24
<211> LENGTH: 7926
<212> TYPE: DNA
<213> ORGANISM: Artificial Sequence
<220> FEATURE:
<223> OTHER INFORMATION: serA overexpression plasmid

<400> SEQUENCE: 24

| | | | | | |
|---|---|---|---|---|---|
| gaattttgcg | gccgcttcga | aagctgtaat | ataaaaacct | tcttcaacta | acggggcagg | 60 |
| ttagtgacat | tagaaaaccg | actgtaaaaa | gtacagtcgg | cattatctca | tattataaaa | 120 |
| gccagtcatt | aggcctatct | gacaattcct | gaatagagtt | cataaacaat | cctgcatgat | 180 |
| aaccatcaca | aacagaatga | tgtacctgta | aagatagcgg | taaatatatt | gaattacctt | 240 |
| tattaatgaa | ttttcctgct | gtaataatgg | gtagaaggta | attactatta | ttattgatat | 300 |
| ttaagttaaa | cccagtaaat | gaagtccatg | gaataataga | aagagaaaaa | gcattttcag | 360 |
| gtataggtgt | tttgggaaac | aatttccccg | aaccattata | tttctctaca | tcagaaaggt | 420 |
| ataaatcata | aaactctttg | aagtcattct | ttacaggagt | ccaaatacca | gagaatgttt | 480 |
| tagatacacc | atcaaaaatt | gtataaagtg | gctctaactt | atcccaataa | cctaactctc | 540 |
| cgtcgctatt | gtaaccagtt | ctaaaagctg | tatttgagtt | tatcacccct | gtcactaaga | 600 |
| aaataaatgc | agggtaaaat | ttatatcctt | cttgttttat | gtttcggtat | aaaacactaa | 660 |
| tatcaatttc | tgtggttata | ctaaaagtcg | tttgttggtt | caaataatga | ttaaatatct | 720 |
| cttttctctt | ccaattgtct | aaatcaattt | tattaaagtt | catttgatat | gcctcctaaa | 780 |
| tttttatcta | aagtgaattt | aggaggctta | cttgtctgct | ttcttcatta | gaatcaatcc | 840 |
| ttttttaaaa | gtcaatatta | ctgtaacata | aatatatatt | ttaaaaatat | cccactttat | 900 |
| ccaattttcg | tttgttgaac | taatgggtgc | tttagttgaa | gaataaagac | cacattaaaa | 960 |
| aatgtggtct | tttgtgtttt | tttaaaggat | ttgagcgtag | cgaaaaatcc | ttttctttct | 1020 |
| tatcttgata | ataagggtaa | ctattgaatt | cggtaccaag | agtttgtaga | aacgcaaaaa | 1080 |
| ggccatccgt | caggatggcc | ttctgcttaa | tttgatgcct | ggcagtttat | ggcgggcgtc | 1140 |
| ctgcccgcca | ccctccgggc | cgttgcttcg | caacgttcaa | atccgctccc | ggcggatttg | 1200 |
| tcctactcag | gagagcgttc | accgacaaac | aacagataaa | acgaaaggcc | cagtcttttcg | 1260 |
| actgagcctt | tcgttttatt | tgatgcctgg | cagttcccta | ctctcgcatg | ggagaccccc | 1320 |
| acactaccat | cggcgctacg | gcgtttcact | tctgagttcg | gcatggggtc | aggtgggacc | 1380 |
| accgcgctac | tgccgccagg | caaattctgt | tttatcagac | cgcttctgcg | ttctgattta | 1440 |
| atctgtatca | ggctgaaaat | cttctctcat | ccgccaaaac | aggatccaat | tatggcagat | 1500 |
| caatgagctt | cacagacaca | atatcaggga | catttgttag | ttctttcaca | attttatctt | 1560 |
| ccagatgtct | gtcaaaggaa | agcatcatga | tggcttctcc | gccttttttcc | ttacggccaa | 1620 |
| cctgcatagt | tgcaatgtta | atatcattat | ctccgagaat | acgtcctact | cggccgatga | 1680 |
| cacctgttgt | atcttgatgc | tggatataca | ccaagtgacc | agtcggataa | aaatcaatat | 1740 |
| taaatccatt | gatctcgaca | attcgttctc | cgaaatgagg | aatatacgta | gccgttacag | 1800 |
| taaaggtgct | gcggtctcct | gtcactttta | cgctgatgca | gttatcgtat | ccagattcag | 1860 |
| aagaggaaat | tttttcactg | aagctaatgc | gcgttctttt | tgcgacaccc | ccggcattga | 1920 |
| cctcattaac | agtagagtct | acgcgcggtt | taaaaagcc | tgacagaagg | gcttttgtaa | 1980 |
| tgaacgatgt | ttcaagttta | gcaattgtgc | cttcatattg | aatggcaaca | tcctgtactg | 2040 |
| gttctttcat | gcactgtgat | acaaggctgc | caatttttcc | tgcaatttga | tggtaaggct | 2100 |

```
taatttttagc aaattcatct tttgtcatgg caggcaggtt gatagctgac atgacaggca    2160
ggccttttgc gaactgcaga acttcttctg acacttgggc ggcgacattg agctgtgctt    2220
ctttcgttga tgctcccaag tgaggagtgg caatgactaa tggatgatca acaagtttgt    2280
tgtcaactgg cggttcgact tcgaaaacgt caagcgctgc tcccgcaaca tgcccgtttt    2340
ccaaagcttc gagaagtgct gcttcatcga taattccgcc tcgcgcacag ttaattaagc    2400
gaacgccttt tttcgttttt gcaatcgttt ctttattcaa taagccttttt gtttcttttg    2460 ttaaaggcgt gtgaacggta atgatatccg cactttcaag cacttcttca aatgtacggc    2520
tgtttacgcc gattttttc gctctttctt ccgttaagaa aggatcaaaa acgtgcacag    2580
tcataccgaa cgctcctcga cgctgtgcaa tttcacttcc gattcggcct aatcctacaa    2640
taccaagcgt ttttccataa agctctgaac cgacataagc tgtgcggttc cactctctgg    2700
atttcactga gatattagcc tgcggaatgt gtctcattaa agaagagatc attgcaaatg    2760
tatgctcagc tgtcgaaatg gtgttgccgt tcggagcatt gatcacgatt accccgtgtt    2820
tcgtagcctc atcaatatcg atattatcga caccgacacc ggctcttccg acaatttta    2880 aagaagtcat tttgttgaaa aggtcttctg ttacttttgt cgcgcttcgc accaaaagag    2940
catcaaaagt atgtaattca tcttctgcat ctgctacgtt tttttgaacg atttcaataa    3000
agtctgattc aataagtggc tgtaaaccgt cgttgctcat tttgtctgag accaatactc    3060
gaaacatgtt ttctcctcct ctagagcgtc ctgctgttgt taagattatt ataccacacc    3120
ttgtagataa agtcaacaac tttttgcaaa atttttcagg aattttagca gaggttgttc    3180
tggatgtaga acaaaacatc tttccgctct tgtgctgtta ggatatcttt cttggaagct    3240
aggtaggcct cgagttatgg cagttggtta aaaggaaaca aaaagaccgt tttcacacaa    3300
aacggtcttt ttcgatttct ttttacagtc acagccactt ttgcaaaaac cggacagctt    3360
catgccttat aactgctgtt tcggtcgaca agcttcgcga agcggccgca aaattcactg    3420
gccgtcgttt tacaacgtcg tgactgggaa acccctggcg ttacccaact taatcgcctt    3480
gcagcacatc cccctttcgc cagctggcgt aatagcgaag aggcccgcac cgatcgccct    3540
tcccaacagt tgcgcagcct gaatggcgaa tggcgcctga tgcggtattt tctccttacg    3600
catctgtgcg gtatttcaca ccgcatatgg tgcactctca gtacaatctg ctctgatgcc    3660
gcatagttaa gccagccccg acacccgcca cacccgctg actatgcttg taaaccgttt    3720
tgtgaaaaaa tttttaaaat aaaaaagggg acctctaggg tccccaatta attagtaata    3780
taatctatta aaggtcattc aaaaggtcat ccaccggatc agcttagtaa agccctcgct    3840 agatttttaat gcggatgttg cgattacttc gccaactatt gcgataacaa gaaaaagcca    3900
gcctttcatg atatatctcc caatttgtgt agggcttatt atgcacgctt aaaaataata    3960
aaagcagact tgacctgata gtttggctgt gagcaattat gtgcttagtg catctaacgc    4020
ttgagttaag ccgcgccgcg aagcggcgtc ggcttgaacg aattgttaga cattatttgc    4080
cgactacctt ggtgatctcg cctttcacgt agtggacaaa ttcttccaac tgatctgcgc    4140
gcgaggccaa gcgatcttct tcttgtccaa gataagcctg tctagcttca agtatgacgg    4200
gctgatactg ggccggcagg cgctccattg cccagtcggc agcgacatcc ttcggcgcga    4260
ttttgccggt tactgcgctg taccaaatgc gggacaacgt aagcactaca tttcgctcat    4320
cgccagccca gtcgggcggc gagttccata gcgttaaggt ttcatttagc gcctcaaata    4380
gatcctgttc aggaaccgga tcaaagagtt cctccgccgc tggacctacc aaggcaacgc    4440
tatgttctct tgcttttgtc agcaagatag ccagatcaat gtcgatcgtg gctggctcga    4500
```

```
agatacctgc aagaatgtca ttgcgctgcc attctccaaa ttgcagttcg cgcttagctg    4560
gataacgcca cggaatgatg tcgtcgtgca caacaatggt gacttctaca gcgcggagaa    4620
tctcgctctc tccaggggaa gccgaagttt ccaaaaggtc gttgatcaaa gctcgccgcg    4680
ttgtttcatc aagccttacg gtcaccgtaa ccagcaaatc aatatcactg tgtggcttca    4740
ggccgccatc cactgcggag ccgtacaaat gtacggccag caacgtcggt tcgagatggc    4800
gctcgatgac gccaactacc tctgatagtt gagtcgatac ttcggcgatc accgcttccc    4860
tcatgatgtt taactttgtt ttagggcgac tgccctgctg cgtaacatcg ttgctgctcc    4920
ataacatcaa acatcgaccc acggcgtaac gcgcttgctg cttggatgcc cgaggcatag    4980 actgtaccc aaaaaaacag tcataacaag ccatgaaaac cgccactgcg ccgttaccac    5040
cgctgcgttc ggtcaaggtt ctggaccagt tgcgtgagcg catacgctac ttgcattaca    5100
gcttacgaac cgaacaggct tatgtccact gggttcgtgc cttcatccgt ttccacggtg    5160
tgcgtcaccc ggcaaccttg ggcagcagcg aagtcgaggc atttctgtcc tggctggcga    5220
acgagcgcaa ggtttcggtc tccacgcatc gtcaggcatt ggcggccttg ctgttcttct    5280
acggcaaggt gctgtgcacg gatctgccct ggcttcagga gatcggaaga cctcggccgt    5340
cgcggcgctt gccggtggtg ctgaccccgg atgaagtggt tcgcatcctc ggttttctgg    5400
aaggcgagca tcgtttgttc gcccagcttc tgtatggaac gggcatgcgg atcagtgagg    5460
gtttgcaact gcgggtcaag gatctggatt cgatcacgg cacgatcatc gtgcgggagg    5520
gcaagggctc caaggatcgg gccttgatgt tacccgagag cttggcaccc agcctgcgcg    5580
agcaggggaa ttgatccggt ggatgaccctt ttgaatgacc tttaatagat tatattacta    5640
attaattggg gaccctagag gtcccctttt ttattttaaa aatttttttca caaaacggtt    5700 tacaagcata acgggttttg ctgcccgcaa acgggctgtt ctggtgttgc tagtttgtta    5760
tcagaatcgc agatccggct tcaggtttgc cggctgaaag cgctatttct tccagaattg    5820
ccatgatttt ttccccacgg gaggcgtcac tggctcccgt gttgtcggca gctttgattc    5880
gataagcagc atcgcctgtt tcaggctgtc tatgtgtgac tgttgagctg taacaagttg    5940
tctcaggtgt tcaatttcat gttctagttg ctttgtttta ctggtttcac ctgttctatt    6000
aggtgttaca tgctgttcat ctgttacatt gtcgatctgt tcatggtgaa cagctttaaa    6060
tgcaccaaaa actcgtaaaa gctctgatgt atctatcttt tttacaccgt tttcatctgt    6120
gcatatggca agttttccct ttgatatcta acggtgaaca gttgttctac ttttgtttgt    6180
tagtcttgat gcttcactga tagatacaag agccataaga acctcagatc cttccgtatt    6240
tagccagtat gttctctagt gtggttcgtt gtttttgcgt gagccatgag aacgaaccat    6300
tgagatcatg cttactttgc atgtcactca aaaattttgc ctcaaaactg gtgagctgaa    6360
tttttgcagt taaagcatcg tgtagtgttt ttcttagtcc gttacgtagg taggaatctg    6420
atgtaatggt tgttggtatt ttgtcaccat tcatttttat ctggttgttc tcaagttcgg    6480
ttacgagatc catttgtcta tctagttcaa cttggaaaat caacgtatca gtcgggcggc    6540
ctcgcttatc aaccaccaat ttcatattgc tgtaagtgtt taaatctta cttattggtt    6600 tcaaacccca ttggttaagc cttttaaact catggtagtt atttcaagc attaacatga    6660 acttaaattc atcaaggcta atctctatat ttgccttgtg agttttcttt tgtgttagtt    6720
cttttaataa ccactcataa atcctcatag agtatttgtt ttcaaaagac ttaacatgtt    6780
ccagattata ttttatgaat ttttttaact ggaaaagata aggcaatatc tcttcactaa    6840
```

```
aaactaattc taattttttcg cttgagaact tggcatagtt tgtccactgg aaaatctcaa    6900
agcctttaac caaaggattc ctgatttcca cagttctcgt catcagctct ctggttgctt    6960
tagctaatac accataagca ttttccctac tgatgttcat catctgagcg tattggttat    7020
aagtgaacga taccgtccgt tctttccttg tagggttttc aatcgtgggg ttgagtagtg    7080
ccacacagca taaaattagc ttggtttcat gctccgttaa gtcatagcga ctaatcgcta    7140
gttcatttgc tttgaaaaca actaattcag acatacatct caattggtct aggtgatttt    7200
aatcactata ccaattgaga tgggctagtc aatgataatt actagtcctt ttcctttgag    7260
ttgtgggtat ctgtaaattc tgctagacct ttgctggaaa acttgtaaat tctgctagac    7320
cctctgtaaa ttccgctaga cctttgtgtg tttttttgt ttatattcaa gtggttataa    7380
tttatagaat aaagaaagaa taaaaaaaga taaaagaat agatcccagc cctgtgtata    7440
actcactact ttagtcagtt ccgcagtatt acaaaggat gtcgcaaacg ctgtttgctc    7500
ctctacaaaa cagaccttaa acccctaaag cttaagtag caccctcgca agctcgggca    7560
aatcgctgaa tattccttttt gtctccgacc atcaggcacc tgagtcgctg tcttttttcgt    7620 gacattcagt tcgctgcgct cacggctctg cagtgaatg ggggtaaatg gcactacagg    7680
cgccttttat ggattcatgc aaggaaacta cccataatac aagaaaagcc cgtcacgggc    7740
ttctcagggc gttttatggc gggtctgcta tgtggtgcta tctgactttt tgctgttcag    7800
cagttcctgc cctctgattt tccagtctga ccacttcgga ttatcccgtg acaggtcatt    7860
cagactggct aatgcaccca gtaaggcagc ggtatcatca acaggcttac ccgtcttact    7920
gtcaac                                                               7926
```

<210> SEQ ID NO 25
<211> LENGTH: 7701
<212> TYPE: DNA
<213> ORGANISM: Artificial Sequence
<220> FEATURE:
<223> OTHER INFORMATION: glyA overexpression plasmid

<400> SEQUENCE: 25

```
gaattttgcg gccgcttcga aagctgtaat ataaaaacct tcttcaacta acggggcagg     60
ttagtgacat tagaaaaccg actgtaaaaa gtacagtcgg cattatctca tattataaaa    120
gccagtcatt aggcctatct gacaattcct gaatagagtt cataaacaat cctgcatgat    180
aaccatcaca aacagaatga tgtacctgta aagatagcgg taaatatatt gaattacctt    240
tattaatgaa ttttcctgct gtaataatgg gtagaaggta attactatta ttattgatat    300
ttaagttaaa cccagtaaat gaagtccatg gaataataga aagagaaaaa gcattttcag    360
gtataggtgt tttgggaaac aatttccccg aaccattata tttctctaca tcagaaaggt    420
ataaatcata aaactctttg aagtcattct ttacaggagt ccaaatacca gagaatgttt    480
tagatacacc atcaaaaatt gtataaagtg gctctaactt atcccaataa cctaactctc    540
cgtcgctatt gtaaccagtt ctaaaagctg tatttgagtt tatcacccct tgtcactaaga    600 aaataaatgc agggtaaaat ttatatcctt cttgtttttat gtttcggtat aaaacactaa    660
tatcaatttc tgtggttata ctaaaagtcg tttgttggtt caaataatga ttaaatatct    720
cttttctctt ccaattgtct aaatcaattt tattaaagtt catttgatat gcctcctaaa    780
tttttatcta aagtgaattt aggaggctta cttgtctgct tcttcatta gaatcaatcc    840 tttttttaaaa gtcaatatta ctgtaacata atatatatt ttaaaatat cccactttat    900 ccaattttcg tttgttgaac taatgggtgc tttagttgaa gaataaagac cacattaaaa    960
```

```
aatgtggtct tttgtgtttt tttaaaggat ttgagcgtag cgaaaaatcc ttttctttct   1020
tatcttgata ataagggtaa ctattgaatt cggtaccaag agtttgtaga aacgcaaaaa   1080
ggccatccgt caggatggcc ttctgcttaa tttgatgcct ggcagtttat ggcgggcgtc   1140
ctgcccgcca ccctccgggc cgttgcttcg caacgttcaa atccgctccc ggcggatttg   1200
tcctactcag gagagcgttc accgacaaac aacagataaa acgaaaggcc cagtctttcg   1260
actgagcctt tcgtttatt tgatgcctgg cagttccta ctctcgcatg gggagacccc    1320
acactaccat cggcgctacg gcgtttcact tctgagttcg gcatggggtc aggtgggacc   1380
accgcgctac tgccgccagg caaattctgt tttatcagac cgcttctgcg ttctgattta   1440
atctgtatca ggctgaaaat cttctctcat ccgccaaaac aggatccccc atcaacaatt   1500
acacacttct attgattcta caaaaaaaga cattgagttt caagaacatc gtcaaaaaac   1560
ccgccgggca taagcccaag cgggttttag gatcttaata atctaattct ttatataaag   1620
gaaatttatc agtcagagca gctacacgct gtcttgcttc ttcaagtttt ccttcatctt   1680
cgtggttttt caatgcaagc gcaatgatag caccgacttc ttctaatgcg tctccgtcaa   1740
aaccgcggct ggttacagca gctgtaccaa gacggatgcc gcttgttacg aaaggttttt   1800
caggatcata tggaatcgcg ttttttgttag acgtaatacc aatttcatca agtacatgct   1860
ccgcaacctt accagtcagt ccgagcgaac gaaggtcaac aaggataagg tggttgtctg   1920
ttccgcctga aacagctgg atgccctctt tcgttaaggc ttcagccaga cgtttcgcgt    1980
ttgaaatgac gttttgtgca tatgttttga atcgtcctg caatacttca ccgaatgaaa    2040
cagcttttgc ggcaataacg tgcatcagag ggccgccttg aattccaggg aagatcgatt   2100
tatcaatttt cttgccaaac tcttcacggc aaaggatcat accgccgcga ggaccgcgaa   2160
gtgttttatg tgttgttgtt gtaacgaaat cagcgtaagg aaccgggttt ggatgaaggc   2220
ctgccgcaac aagtcctgcg atatgtgcca tatccaccat gaagtaagcg ccgacttcat   2280
cagcaatttc acggaatttc ttaaagtcga ttgtacgagg atacgcactt gctcctgcta   2340
cgataagctt cggtttatga gcgagggctt tttcacgcac gtcatcgtaa tcaatatatt   2400
gagtttcttt atctacgccg tactcaacaa agttatattg aacaccgctg aagttgactg   2460
ggcttccgtg tgttaaatgg ccgccgtggg agaggttcat cccaagtaca gtatcgcctt   2520
gctccaaaat cgtgaagtac actgccatgt ttgcttgtgc gcctgaatga ggctgaacgt   2580
ttacatgctc cgctccaaag atttccttcg cgcggtcacg ggcgatatct tcaacgacat   2640
cgacgtgctc gcatccgccg tagtagcgtt tgcccggata tccttctgcg tacttatttg   2700
tcaaaacaga tccttgtgct tccataaccg cttcacttac aaagttctca gaagcaatca   2760
attcgatctt agtctgttgg cgttcacgct catttttaat ggcgttaaac acttgttcgt   2820
cttgcgcagg taaatgtttc atgtttacac ctcctctaga gcgtcctgct gttgttaaga   2880
ttattatacc acaccttgta gataaagtca acaactttt gcaaaatttt tcaggaattt    2940
tagcagaggt tgttctggat gtagaacaaa acatctttcc gctcttgtgc tgttaggata   3000
tctttcttgg aagctaggta ggcctcgagt tatggcagtt ggttaaaagg aaacaaaaag   3060
accgttttca cacaaaacgg tcttttttcga tttctttta cagtcacagc cacttttgca    3120 aaaccggac agcttcatgc cttataactg ctgtttcggt cgacaagctt cgcgaagcgg   3180
ccgcaaaatt cactggccgt cgttttacaa cgtcgtgact gggaaaaccc tggcgttacc   3240
caacttaatc gccttgcagc acatccccct ttcgccagct ggcgtaatag cgaagaggcc   3300
```

-continued

```
cgcaccgatc gcccttccca acagttgcgc agcctgaatg gcgaatggcg cctgatgcgg    3360
tattttctcc ttacgcatct gtgcggtatt tcacaccgca tatggtgcac tctcagtaca    3420
atctgctctg atgccgcata gttaagccag ccccgacacc cgccaacacc cgctgactat    3480
gcttgtaaac cgttttgtga aaaatttttt aaaataaaaa aggggacctc tagggtcccc    3540
aattaattag taatataatc tattaaaggt cattcaaaag gtcatccacc ggatcagctt    3600
agtaaagccc tcgctagatt ttaatgcgga tgttgcgatt acttcgccaa ctattgcgat    3660
aacaagaaaa agccagcctt tcatgatata tctcccaatt tgtgtagggc ttattatgca    3720
cgcttaaaaa taataaaagc agacttgacc tgatagtttg gctgtgagca attatgtgct    3780
tagtgcatct aacgcttgag ttaagccgcg ccgcgaagcg cgtcggctt gaacgaattg     3840
ttagacatta tttgccgact accttggtga tctcgccttt cacgtagtgg acaaattctt    3900
ccaactgatc tgcgcgcgag gccaagcgat cttcttcttg tccaagataa gcctgtctag    3960
cttcaagtat gacgggctga tactgggccg gcaggcgctc cattgcccag tcggcagcga    4020
catccttcgg cgcgattttg ccggttactg cgctgtacca aatgcgggac aacgtaagca    4080
ctacatttcg ctcatcgcca gcccagtcgg cggcgagtt ccatagcgtt aaggtttcat     4140
ttagcgcctc aaatagatcc tgttcaggaa ccggatcaaa gagttcctcc gccgctggac    4200
ctaccaaggc aacgctatgt tctcttgctt ttgtcagcaa gatagccaga tcaatgtcga    4260
tcgtggctgg ctcgaagata cctgcaagaa tgtcattgcg ctgccattct ccaaattgca    4320
gttcgcgctt agctggataa cgccacggaa tgatgtcgtc gtgcacaaca atggtgactt    4380
ctacagcgcg gagaatctcg ctctctccag gggaagccga agtttccaaa aggtcgttga    4440
tcaaagctcg ccgcgttgtt tcatcaagcc ttacggtcac cgtaaccagc aaatcaatat    4500
cactgtgtgg cttcaggccg ccatccactg cggagccgta caaatgtacg ccagcaacg    4560
tcggttcgag atggcgctcg atgacgccaa ctacctctga tagttgagtc gatacttcgg    4620
cgatcaccgc ttccctcatg atgtttaact ttgttttagg gcgactgccc tgctgcgtaa    4680
catcgttgct gctccataac atcaaacatc gacccacggc gtaacgcgct tgctgcttgg    4740
atgcccgagg catagactgt accccaaaaa aacagtcata acaagccatg aaaaccgcca    4800
ctgcgccgtt accaccgctg cgttcggtca aggttctgga ccagttgcgt gagcgcatac    4860
gctacttgca ttacagctta cgaaccgaac aggcttatgt ccactgggtt cgtgccttca    4920
tccgtttcca cggtgtgcgt cacccggcaa ccttgggcag cagcgaagtc gaggcatttc    4980
tgtcctggct ggcgaacgag cgcaaggttt cggtctccac gcatcgtcag gcattggcgg    5040
ccttgctgtt cttctacggc aaggtgctgt gcacggatct gccctggctt caggagatcg    5100
gaagacctcg gccgtcgcgg cgcttgccgg tggtgctgac cccggatgaa gtggttcgca    5160
tcctcggttt tctggaaggc gagcatcgtt tgttcgccca gcttctgtat ggaacgggca    5220
tgcggatcag tgagggtttg caactgcggg tcaaggatct ggatttcgat cacggcacga    5280
tcatcgtgcg ggagggcaag ggctccaagg atcgggcctt gatgttaccc gagagcttgg    5340
cacccagcct gcgcgagcag gggaattgat ccggtggatg acctttgaa tgacctttaa     5400
tagattatat tactaattaa ttggggaccc tagaggtccc cttttttatt ttaaaaattt    5460
tttcacaaaa cggtttacaa gcataacggg ttttgctgcc cgcaaacggg ctgttctggt    5520
gttgctagtt tgttatcaga atcgcagatc cggcttcagg tttgccggct gaaagcgcta    5580
tttcttccag aattgccatg attttttccc cacgggaggc gtcactggct cccgtgttgt    5640
cggcagcttt gattcgataa gcagcatcgc ctgtttcagg ctgtctatgt gtgactgttg    5700
```

```
agctgtaaca agttgtctca ggtgttcaat ttcatgttct agttgctttg ttttactggt    5760
ttcacctgtt ctattaggtg ttacatgctg ttcatctgtt acattgtcga tctgttcatg    5820
gtgaacagct ttaaatgcac caaaaactcg taaaagctct gatgtatcta tcttttttac    5880
accgttttca tctgtgcata tggacagttt tcccttttgat atctaacggt gaacagttgt   5940
tctacttttg tttgttagtc ttgatgcttc actgatagat acaagagcca taagaacctc    6000
agatccttcc gtatttagcc agtatgttct ctagtgtggt tcgttgtttt tgcgtgagcc    6060
atgagaacga accattgaga tcatgcttac tttgcatgtc actcaaaaat tttgcctcaa    6120
aactggtgag ctgaattttt gcagttaaag catcgtgtag tgttttttctt agtccgttac   6180
gtaggtagga atctgatgta atggttgttg gtattttgtc accattcatt tttatctggt    6240
tgttctcaag ttcggttacg agatccattt gtctatctag ttcaacttgg aaaatcaacg    6300
tatcagtcgg gcggcctcgc ttatcaacca ccaatttcat attgctgtaa gtgtttaaat    6360
ctttacttat tggtttcaaa acccattggt taagccttttt aaactcatgg tagttattttt  6420
caagcattaa catgaactta aattcatcaa ggctaatctc tatatttgcc ttgtgagttt    6480
tcttttgtgt tagttctttt aataaccact cataaatcct catagagtat ttgttttcaa    6540
aagacttaac atgttccaga ttatatttta tgaattttt taactggaaa agataaggca     6600
atatctcttc actaaaaact aattctaatt tttcgcttga gaacttggca tagtttgtcc    6660
actggaaaat ctcaaagcct ttaaccaaag gattcctgat ttccacagtt ctcgtcatca    6720
gctctctggt tgctttagct aatacaccat aagcattttc cctactgatg ttcatcatct    6780
gagcgtattg gttataagtg aacgataccg tccgttcttt ccttgtaggg ttttcaatcg    6840
tggggttgag tagtgccaca cagcataaaa ttagcttggt ttcatgctcc gttaagtcat    6900
agcgactaat cgctagttca tttgctttga aaacaactaa ttcagacata catctcaatt    6960
ggtctaggtg atttttaatca ctataccaat tgagatgggc tagtcaatga taattactag   7020
tccttttcct ttgagttgtg ggtatctgta aattctgcta gacctttgct ggaaaacttg    7080
taaattctgc tagaccctct gtaaattccg ctagaccttt gtgtgttttt tttgtttata    7140
ttcaagtggt tataatttat agaataaaga aagaataaaa aaagataaaa agaatagatc    7200
ccagccctgt gtataactca ctactttagt cagttccgca gtattacaaa aggatgtcgc    7260
aaacgctgtt tgctcctcta caaaacagac cttaaaaccc taaaggctta agtagcaccc    7320
tcgcaagctc gggcaaatcg ctgaatattc cttttgtctc cgaccatcag gcacctgagt    7380
cgctgtcttt ttcgtgacat tcagttcgct gcgctcacgg ctctggcagt gaatgggggt    7440
aaatggcact acaggcgcct tttatggatt catgcaagga aactacccat aatacaagaa    7500
aagcccgtca cgggcttctc agggcgtttt atggcgggtc tgctatgtgg tgctatctga    7560
cttttttgctg ttcagcagtt cctgccctct gattttccag tctgaccact tcggattatc    7620
ccgtgacagg tcattcagac tggctaatgc acccagtaag gcagcggtat catcaacagg    7680
cttacccgtc ttactgtcaa c                                              7701
```

MICROORGANISMS AND PROCESSES FOR ENHANCED PRODUCTION OF PANTOTHENATE

RELATED APPLICATIONS

This application is a national phase application of PCT/US02/00925, filed Jan. 18, 2002, which claims the benefit of prior-filed provisional Patent Application Ser. No. 60/347,638, entitled "Microorganisms and Processes for Enhanced Production of Pantothenate", filed Jan. 11, 2002 (expired), to prior-filed provisional Patent Application Ser. No. 60/263,053, filed Jan. 19, 2001 (expired), and to prior-filed provisional Patent Application Ser. No. 60/262,995, filed Jan. 19, 2001 (expired). The present invention is also related to U.S. patent application Ser. No.10/984,449, filed Nov. 8, 2004, which is a continuation of Ser. No. 09/667,569, filed Sep. 21, 2000 (abandoned), which is a continuation-in-part of U.S. patent application Ser. No. 09/400,494, filed Sep. 21, 1999 (abandoned). U.S. patent application Ser. No. 09/667,569 also claims the benefit of prior-filed provisional Patent Application Ser. No. 60/210,072, filed Jun. 7, 2000 (expired), provisional Patent Application Ser. No. 60/221,836, filed Jul. 28, 2000 (expired), and provisional Patent Application Ser. No. 60/227,860, filed Aug. 24, 2000 (expired). The entire content of each of the above-referenced applications is incorporated herein by this reference.

BACKGROUND OF THE INVENTION

Pantothenate, also known as pantothenic acid or vitamin B5, is a member of the B complex of vitamins and is a nutritional requirement for mammals, including livestock and humans (e.g., from food sources, as a water soluble vitamin supplement or as a feed additive). In cells, pantothenate is used primarily for the biosynthesis of coenzyme A (CoA) and acyl carrier protein (ACP). These coenzymes function in the metabolism of acyl moieties which form thioesters with the sulfhydryl group of the 4'-phosphopantetheine portion of these molecules. These coenzymes are essential in all cells, participating in over 100 different intermediary reactions in cellular metabolism.

The conventional means of synthesizing pantothenate (in particular, the bioactive D isomer) is via chemical synthesis from bulk chemicals, a process which is hampered by excessive substrate cost as well as the requirement for optical resolution of racemic intermediates. Accordingly, researchers have recently looked to bacterial or microbial systems that produce enzymes useful in pantothenate biosynthesis processes (as bacteria are themselves capable of synthesizing pantothenate). In particular, bioconversion processes have been evaluated as a means of favoring production of the preferred isomer of pantothenic acid. Moreover, methods of direct microbial synthesis have recently been examined as a means of facilitating D-pantothenate production.

There is still, however, significant need for improved pantothenate production processes, in particular, for microbial processes optimized to produce higher yields of desired product.

SUMMARY OF THE INVENTION

The present invention relates to improved processes (e.g., microbial syntheses) for the production of pantothenate. Pantothenate production processes have been described in related applications which feature, for example, microbes engineered to overexpress key enzymes of the pantothenate biosynthetic pathway and the isoleucine-valine biosynthetic pathway (see e.g., FIG. 1). Strains have been engineered that are capable of producing >50 g/l of pantothenate in standard fermentation processes (see e.g., International Public. No. WO 01/21772 and U.S. Patent Application No. 60/262,995). In particular, increasing the expression of the panB, panC, panD and panE1 genes and increasing the expression of the ilvBNC and ilvD genes results in strains that convert glucose (pyruvate) to commercially attractive quantities of pantothenate.

In order to enhance production levels of for example, pantothenate, various improvements on the above-described methods have now been developed. For example, U.S. patent application Ser. No. 09/667,569 describes production strains having modified (e.g., deleted or decreased-activity) pantothenate kinase enzymes. In such strains, the pantothenate levels are effectively increased by decreasing utilization of gpantothenate for coenzymeA ("CoA") synthesis. U.S. Patent Application Ser. No. 60/262,995 further describes improved pantothenate-productions strains that have been engineered to minimize utilization of various pantothenate biosynthetic enzymes and/or isoleucine-valine biosynthetic enzymes and/or their respective substrates from being used to produce an alternative product identified as HMBPA.

The present invention features methods to further enhance pantothenate production by modulating a biosynthetic pathway that supplies a substrate for the pantothenate biosynthetic pathway, namely the methylenetetrahydrofolate ("MTF") biosynthetic pathway. In particular, it has been discovered that increasing levels of MTF by modification of the MTF biosynthetic pathway results in enhanced levels of the key pantothenate biosynthetic pathway intermediate, ketopantoate. Enhanced ketopantoate levels, in turn, result in significantly enhanced pantothenate production levels in appropriately engineered strains. In essence, the present inventors have identified a limiting step in the production of panto-compounds (e.g., pantothenate) by strains engineered to overexpress, for example, the panB, panC, panD, panE1, ilvBNC and ilvD genes, and describe herein a means for overcoming this limitation by modification of the MTF biosynthetic pathway.

At least three effective means of modifying the MTF biosynthetic pathway are described herein. In one aspect, it has been demonstrated that increasing serine levels in the culture medium of pantothenate-producing microorganisms results in enhanced panto-compound production. It has also been demonstrated that increasing the synthesis or activity of 3-phosphoglycerate dehydrogenase (the serA gene product), or the synthesis or activity of serine hydroxymethyl transferase (the glyA gene product), thereby enhancing serine and methylenetetrahydrofolate biosynthesis in appropriately engineered microorganisms, increases panto-compound production.

Accordingly, in one aspect the invention features processes for the enhanced production of pantoate and pantothenate that involve culturing microorganisms having modified pantothenate biosynthetic enzyme activities and having modified methylenetetrahydrofolate (MTF) biosynthetic enzyme activities under conditions such that pantothenate production is enhanced. In another aspect the invention features processes for the enhanced production of pantoate and pantothenate that involve culturing microorganisms having modified pantothenate biosynthetic enzyme activities, having modified isoleucine-valine (ilv) biosynthetic enzymes, and having modified methylenetetrahydrofolate (MTF) biosynthetic enzyme activities under conditions such that pantothenate production is enhanced. In particular, the invention features methods for enhancing production of desired products (e.g., pantoate and/or pantothenate) by increasing the levels of a key intermediate, ketopantoate, by enzymes that contribute to its synthesis. Preferred methods result in production of pantothenate at levels greater than 50, 60, 70 or more g/L after 36 hours of culturing the microorganisms, or such that at least 60, 70, 80, 90 or more g/L pantothenate is produced after 36 hours of culturing the microorganisms. Recombinant microorganisms and conditions for culturing same are also are featured. Also featured are compositions produced by such microorganisms.

Other features and advantages of the invention will be apparent from the following detailed description and claims.

BRIEF DESCRIPTION OF THE DRAWINGS

FIG. 3 is a schematic representation of the construction of the plasmid pAN665.

DETAILED DESCRIPTION OF THE INVENTION

The present invention is directed to improved methods for producing panto-compounds (e.g., ketopantoate, pantoate and/or pantothenate) and strains engineered for use in said improved methods. Strains capable of producing >50 g/l of pantothenate can be constructed as taught in International Patent Application Serial No. WO 01/21772 and in U.S. Patent Application Ser. No. 60/262,995. By increasing the expression of the panB, panC, panD and panE1 genes and by increasing the expression of the ilvBNC and ilvD genes, one can design strains (e.g., *Bacillus* strains) that convert glucose (pyruvate) to commercially attractive quantities of pantothenate.

However, it has now been discovered that in strains engineered to express high levels of the panB gene product, ketopantoate hydroxymethyltransferase (e.g., PA824, described in U.S. patent application Ser. No. 09/667,569 and PA668-24, described in U.S. Patent Application Ser. No. 60/262,995), a limiting step for further increases in the production of pantothenate is still the conversion of α-ketoisovalerate (α-KIV) to ketopantoate. Methods to increase the synthesis of α-KIV were described previously in International Patent Application Serial No. WO 01/21772 and U.S. Patent Application Ser. No. 60/262,995. Here we disclose that even further increases in pantothenate production can be achieved by engineering designed to increase the levels of MTF, or the rate of MTF synthesis.

Accordingly, the present invention features modulating the methylenetetrahydrofolate ("MTF") biosynthetic pathway. In particular, increasing MTF levels in panto-compound producing microbes is an effective means of enhancing ketopantoate production, and in turn results in enhanced pantoate and/or pantothenate production in appropriately-engineered recombinant microorganisms.

Figure 1:
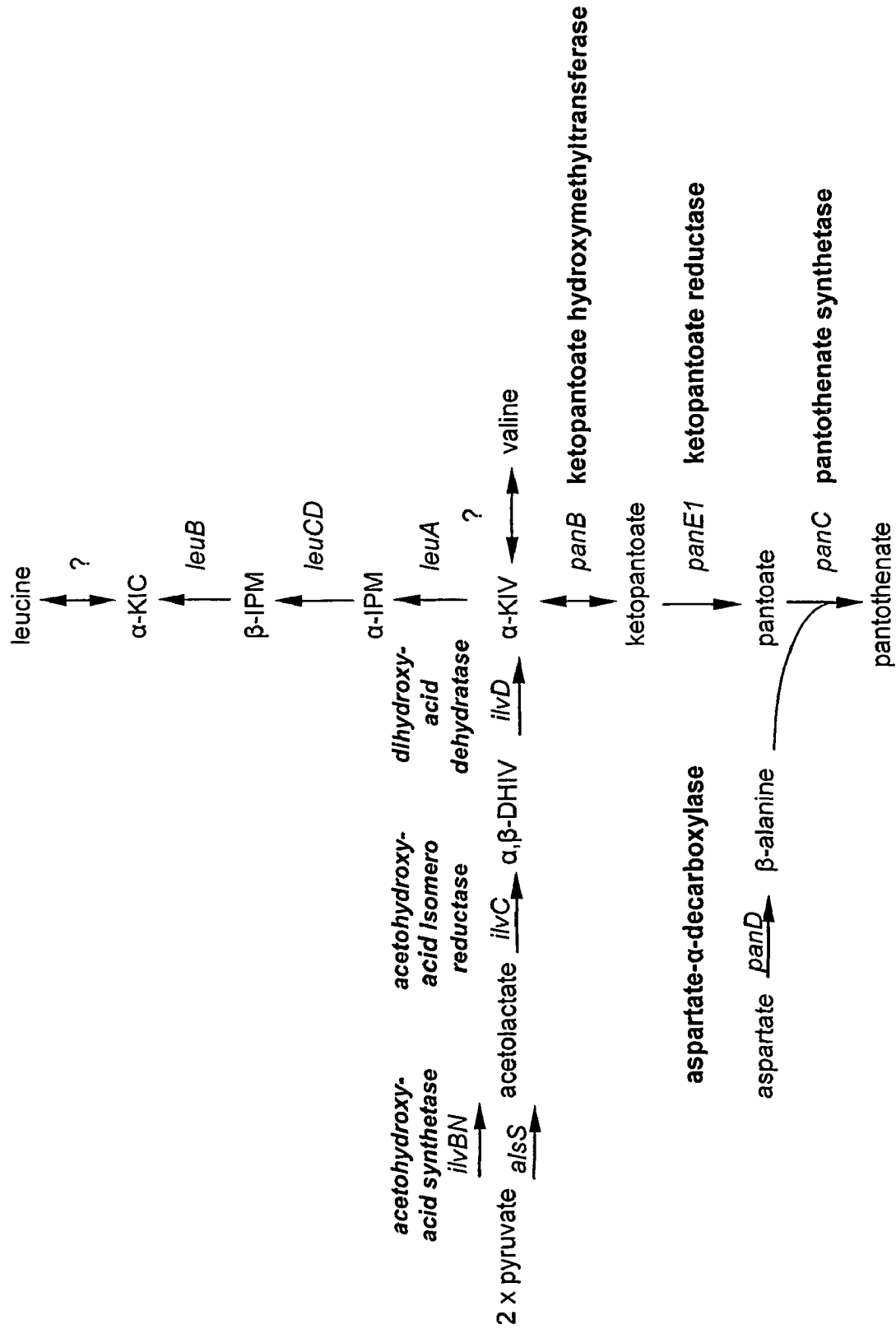
FIG. 1 is a schematic representation of the pantothenate and isoleucine-valine (ilv) biosynthetic pathways. Pantothenate biosynthetic enzymes are depicted in bold and their corresponding genes indicated in italics. Isoleucine-valine (ilv) biosynthetic enzymes are depicted in bold italics and their corresponding genes indicated in italics.

Ketopantoate hydroxymethylenetransferase catalyzes the production of ketopantoate from α-ketoisivalerate ("α-KIV") and MTF (see e.g., FIG. 1). In particular, the enzyme catalyzes the transfer of a hydroxymethyl group from MTF to α-KIV to yield ketopantoate. Both α-KIV and MTF are substrates for this reaction, and their syntheses can be increased in order to improve production of ketopantoate. The pathway for MTF biosynthesis in *E. coli* (and presumably also *Bacillus subtilis*) is outlined in FIG. 2. MTF is synthesized from tetrahydrofolate and serine in a reaction catalyzed by the glyA gene that encodes serine hydroxymethyl transferase. For improved MTF synthesis the cells need increased quantities of both substrates and the product of the glyA gene.

In one embodiment, the invention features processes for the enhanced production of pantothenate that involve culturing a microorganism having (i) a deregulated pantothenate biosynthetic pathway (e.g., having one, two, three or four pantothenate biosynthetic enzymes deregulated) and (ii) a deregulated methylenetetrahydrofolate (MTF) biosynthetic pathway (e.g., having at least one or two MTF biosynthetic enzymes deregulated), under conditions such that pantothenate production is enhanced. Exemplary pantothenate biosynthetic enzymes include ketopantoate hydroxymethyltransferase, ketopantoate reductase, pantothenate synthetase and aspartate-α-decarboxylase. Exemplary MTF biosynthetic enzymes include the serA gene product and the glyA gene product.

In another embodiment, the invention features processes for the enhanced production of pantothenate that involve culturing a microorganism having (i) a deregulated pantothenate biosynthetic pathway (e.g., having one, two, three or four pantothenate biosynthetic enzymes deregulated), (ii) a deregulated isoleucine-valine (ill) biosynthetic pathway (e.g., having one, two or three ilv, biosynthetic enzymes deregulated), and (iii) a deregulated MTF biosynthetic pathway (e.g., having at least one or two MTF biosynthetic enzymes deregulated), under conditions such that pantothenate production is enhanced. Exemplary ilv biosynthetic enzymes include acetohydroxyacid acid synthetase, acetohydroxyacid isomeroreductase, and dihydroxyacid dehydratase.

In another embodiment, the invention features processes for the production of pantothenate that involve culturing a microorganism having a deregulated pantothenate biosynthetic pathway, a deregulated ilv biosynthetic pathway, and a deregulated MTF biosynthetic pathway, deregulated such that at least 50 g/L pantothenate is produced after 36 hours of culturing the microorganism, preferably such that at least 60 g/L pantothenate is produced after 36 hours of culturing the microorganism, and more preferably such that at least 70 g/L pantothenate is produced after 36 hours of culturing the microorganism.

In another embodiment, the invention features processes for the production of pantothenate that involve culturing a microorganism having a deregulated pantothenate biosynthetic pathway, a deregulated ilv biosynthetic pathway, and a deregulated MTF biosynthetic pathway, deregulated such that at least 60 g/L pantothenate is produced after 48 hours of culturing the microorganism, preferably such that at least 70 g/L pantothenate is produced after 48 hours of culturing the microorganism, and more preferably such that at least 80 g/L pantothenate is produced after 48 hours of culturing the microorganism.

The invention further features methods as described above, wherein pantothenate production is further enhanced by regulating pantothenate kinase activity (e.g., wherein pantothenate kinase activity is decreased). In one embodiment, CoaA is deleted and CoaX is downregulated. In another embodiment, CoaX is deleted and CoaA is downregulated. In yet another embodiment, CoaX and CoaA are downregulated. The invention further features methods as described above, wherein the microorganisms are cultured under conditions of excess serine. The invention further features methods as described above, wherein the microorganisms have the pantothenate biosynthetic pathway deregulated such that pantothenate production is independent of β-alanine feed.

Products synthesized according to the processes of the invention are also featured, as are compositions that include pantothenate produced according to said processes. Recombinant microorganisms for use in the processes of the invention are also featured. In one embodiment, the invention features a recombinant microorganism for the enhanced production of pantothenate having a deregulated pantothenate biosynthetic pathway and a deregulated MTF biosynthetic pathway. In another embodiment, the invention features a recombinant microorganism for the enhanced production of pantothenate having a deregulated pantothenate biosynthetic pathway, a deregulated MTF biosynthetic pathway and a deregulated ilv pathway. Microorganisms can further have reduced pantothenate kinase activity. Preferred microorganisms belong to the genus *Bacillus*, for example *Bacillus subtilis*.

As described above, certain aspects of the invention feature processes for the enhanced production of panto-compounds (e.g., pantoate and/or pantothenate) that involve culturing microorganisms having at least a deregulated pantothenate biosynthetic pathway. The term "pantothenate biosynthetic pathway" includes the biosynthetic pathway involving pantothenate biosynthetic enzymes (e.g., polypeptides encoded by biosynthetic enzyme-encoding genes), compounds (e.g., substrates, intermediates or products), cofactors and the like utilized in the formation or synthesis of pantothenate. The term "pantothenate biosynthetic pathway" includes the biosynthetic pathway leading to the synthesis of pantothenate in microorganisms (e.g., in vivo) as well as the biosynthetic pathway leading to the synthesis of pantothenate in vitro.

As used herein, a microorganism "having a deregulated pantothenate biosynthetic pathway" includes a microorganism having at least one pantothenate biosynthetic enzyme deregulated (e.g., overexpressed) (both terms as defined herein) such that pantothenate production is enhanced (e.g., as compared to pantothenate production in said microorganism prior to deregulation of said biosynthetic enzyme or as compared to a wild-type microorganism). The term "pantothenate" includes the free acid form of pantothenate, also referred to as "pantothenic acid" as well as any salt thereof (e.g., derived by replacing the acidic hydrogen of pantothenate or pantothenic acid with a cation, for example, calcium, sodium, potassium, ammonium, magnesium), also referred to as a "pantothenate salt". The term "pantothenate" also includes alcohol derivatives of pantothenate. Preferred pantothenate salts are calcium pantothenate or sodium pantothenate. A preferred alcohol derivative is pantothenol. Pantothenate salts and/or alcohols of the present invention include salts and/or alcohols prepared via conventional methods from the free acids described herein. In another embodiment, a pantothenate salt is synthesized directly by a microorganism of the present invention. A pantothenate salt of the present invention can likewise be converted to a free acid form of pantothenate or pantothenic acid by conventional methodology. The term "pantothenate" is also abbreviated as "pan" herein.

Preferably, a microorganism "having a deregulated pantothenate biosynthetic pathway" includes a microorganism having at least one pantothenate biosynthetic enzyme deregulated (e.g., overexpressed) such that pantothenate production is 1 g/L or greater. More preferably, a microorganism "having a deregulated pantothenate biosynthetic pathway" includes a microorganism having at least one pantothenate biosynthetic enzyme deregulated (e.g., overexpressed) such that pantothenate production is 2 g/L or greater. Even more preferably, a microorganism "having a deregulated pantothenate biosynthetic pathway" includes a microorganism having at least one pantothenate biosynthetic enzyme deregulated (e.g., overexpressed) such that pantothenate production is 10 g/L, 20 g/L, 30 g/L, 40 g/L, 50 g/L, or greater.

The term "pantothenate biosynthetic enzyme" includes any enzyme utilized in the formation of a compound (e.g., intermediate or product) of the pantothenate biosynthetic pathway. For example, synthesis of pantoate from α-ketoisovalerate (α-KIV) proceeds via the intermediate, ketopantoate. Formation of ketopantoate is catalyzed by the pantothenate biosynthetic enzyme PanB or ketopantoate hydroxymethyltransferase (the panB gene product). Formation of pantoate is catalyzed by the pantothenate biosynthetic enzyme PanE1 or ketopantoate reductase (the panE1 gene product). Synthesis of β-alanine from aspartate is catalyzed by the pantothenate biosynthetic enzyme PanD or aspartate-α-decarboxylase (the panD gene product). Formation of pantothenate from pantoate and β-alanine (e.g., condensation) is catalyzed by the pantothenate biosynthetic enzyme PanC or pantothenate synthetase (the panC gene product). Pantothenate biosynthetic enzymes may also perform an alternative function as enzymes in the HMBPA biosynthetic pathway described herein.

Accordingly, in one embodiment, the invention features a process for the enhanced production of pantothenate that includes culturing a microorganism having at least one pantothenate biosynthetic enzyme deregulated (e.g., deregulated such that pantothenate production is enhanced), said enzyme being selected, for example, from the group consisting of PanB (or ketopantoate hydroxymethyltransferase), PanC (or pantothenate synthetase), PanD (or aspartate-α-decarboxylase), PanE1 (or ketopantoate reductase). In another embodiment, the invention features a process for the enhanced production of pantothenate that includes culturing a microorganism having at least two pantothenate biosynthetic enzymes deregulated, said enzymes being selected, for example, from the group consisting of PanB (or ketopantoate hydroxymethyltransferase), PanC (or pantothenate synthetase), PanD (or aspartate-α-decarboxylase), and PanE1 (or ketopantoate reductase). In another embodiment, the invention features a process for the enhanced production of pantothenate that includes culturing a microorganism having at least three pantothenate biosynthetic enzymes deregulated, said enzymes being selected, for example, from the group consisting of PanB (or ketopantoate hydroxymethyltransferase), PanC (or pantothenate synthetase), PanD (or aspartate-α-decarboxylase), and PanE1 (or ketopantoate reductase). In another embodiment, the invention features a process for the enhanced production of pantothenate that includes culturing a microorganism having at least four pantothenate biosynthetic enzymes deregulated, for example, a microorganism having PanB (or ketopantoate hydroxymethyltransferase), PanC (or pantothenate synthetase), PanD (or aspartate-α-decarboxylase), and PanE1 (or ketopantoate reductase) deregulated.

In another aspect, the invention features processes for the enhanced production of pantothenate that involve culturing microorganisms having a deregulated isoleucine-valine biosynthetic pathway. The term "isoleucine-valine biosynthetic pathway" includes the biosynthetic pathway involving isoleucine-valine biosynthetic enzymes (e.g., polypeptides encoded by biosynthetic enzyme-encoding genes), compounds (e.g., substrates, intermediates or products), cofactors and the like utilized in the formation or synthesis of conversion of pyruvate to valine or isoleucine. The term "isoleucine-valine biosynthetic pathway" includes the biosynthetic pathway leading to the synthesis of valine or isoleucine in microorganisms (e.g., in vivo) as well as the biosynthetic pathway leading to the synthesis of valine or isoleucine in vitro.

As used herein, a microorganism "having a deregulated isoleucine-valine (ilv) pathway" includes a microorganism having at least one isoleucine-valine (ilv) biosynthetic enzyme deregulated (e.g., overexpressed) (both terms as defined herein) such that isoleucine and/or valine and/or the valine precursor, α-ketoisovaerate (α-KIV) production is enhanced (e.g., as compared to isoleucine and/or valine and/or α-KIV production in said microorganism prior to deregulation of said biosynthetic enzyme or as compared to a wild-type microorganism). FIG. 1 includes a schematic representation of the isoleucine-valine biosynthetic pathway. Isoleucine-valine biosynthetic enzymes are depicted in bold italics and their corresponding genes indicated in italics. The term "isoleucine-valine biosynthetic enzyme" includes any enzyme utilized in the formation of a compound (e.g., intermediate or product) of the isoleucine-valine biosynthetic pathway. According to FIG. 1, synthesis of valine from pyruvate proceeds via the intermediates, acetolactate, α,β-dihydroxyisovalerate (α,β-DHIV) and α-ketoisovalerate (α-KIV). Formation of acetolactate from pyruvate is catalyzed by the isoleucine-valine biosynthetic enzyme acetohydroxyacid synthetase (the ilvBN gene products, or alternatively the alsS gene product). Formation of α,β-DHIV from acetolactate is catalyzed by the isoleucine-valine biosynthetic enzyme acetohydroxyacid isomeroreductase (the ilvC gene product). Synthesis of α-KIV from α,β-DHIV is catalyzed by the isoleucine-valine biosynthetic enzyme dihydroxyacid dehydratase (the ilvD gene product). Moreover, valine and isoleucine can be interconverted with their respective α-keto compounds by branched chain amino acid transaminases. Isoleucine-valine biosynthetic enzymes may also perform an alternative function as enzymes in the HMBPA biosynthetic pathway described herein.

Accordingly, in one embodiment, the invention features a process for the enhanced production of pantothenate that includes culturing a microorganism having at least one isoleucine-valine (ilv) biosynthetic enzyme deregulated (e.g., deregulated such that valine and/or isoleucine and/or α-KIV production is enhanced), said enzyme being selected, for example, from the group consisting of IlvBN, AlsS (or acetohydroxyacid synthetase), IlvC (or acetohydroxyacid isomeroreductase) and IlvD (or dihydroxyacid dehydratase). In another embodiment, the invention features a process for the enhanced production of pantothenate that includes culturing a microorganism having at least two isoleucine-valine (ilv) biosynthetic enzymes deregulated, said enzyme being selected, for example, from the group consisting of IlvBN, AlsS (or acetohydroxyacid synthetase), IlvC (or acetohydroxyacid isomeroreductase) and IlvD (or dihydroxyacid dehydratase). In another embodiment, the invention features a process for the enhanced production of pantothenate that includes culturing a microorganism having at least three isoleucine-valine (ilv) biosynthetic enzymes deregulated, for example, said microorganism having IlvBN or AlsS (or acetohydroxyacid synthetase), IlvC (or acetohydroxyacid isomeroreductase) and IlvD (or dihydroxyacid dehydratase) deregulated.

As mentioned herein, enzymes of the pantothenate biosynthetic pathway and/or the isoleucine-valine (ilv) pathway have been discovered to have an alternative activity in the synthesis of [R]-3-(2-hydroxy-3-methyl-butyrylamino)-propionic acid ("HMBPA") or the [R]-3-(2-hydroxy-3-methyl-butyrylamino)-propionic acid ("HMBPA") biosynthetic pathway. The term "[R]-3-(2-hydroxy-3-methyl-butyrylamino)-propionic acid ("HMBPA") biosynthetic pathway" includes the alternative biosynthetic pathway involving biosynthetic enzymes and compounds (e.g., substrates and the like) traditionally associated with the pantothenate biosynthetic pathway and/or isoleucine-valine (ilv) biosynthetic pathway utilized in the formation or synthesis of HMBPA. The term "HMBPA biosynthetic pathway" includes the biosynthetic pathway leading to the synthesis of HMBPA in microorganisms (e.g., in vivo) as well as the biosynthetic pathway leading to the synthesis of HMBPA in vitro.

The term "HMBPA biosynthetic enzyme" includes any enzyme utilized in the formation of a compound (e.g., intermediate or product) of the HMBPA biosynthetic pathway. For example, synthesis of 2-hydroxyisovaleric acid (α-HIV) from α-ketoisovalerate (α-KIV) is catalyzed by the panE1 or panE2 gene product (PanE1 is alternatively referred to herein as ketopantoate reductase) and/or is catalyzed by the ilvC gene product (alternatively referred to herein as acetohydroxyacid isomeroreductase). Formation of HMBPA from β-alanine and α-HIV is catalyzed by the panC gene product (alternatively referred to herein as pantothenate synthetase).

The term "[R]-3-(2-hydroxy-3-methyl-butyrylamino)-propionic acid ("HMBPA")" includes the free acid form of HMBPA, also referred to as "[R]-3-(2-hydroxy-3-methyl-butyrylamino)-propionate" as well as any salt thereof (e.g., derived by replacing the acidic hydrogen of 3-(2-hydroxy-3-methyl-butyrylamino)-propionic acid or 3-(2-hydroxy-3-methyl-butyrylamino)-propionate with a cation, for example, calcium, sodium, potassium, ammonium, magnesium), also referred to as a "3-(2-hydroxy-3-methyl-butyrylamino)-propionic acid salt" or "HMBPA salt". Preferred HMBPA salts are calcium HMBPA or sodium HMBPA. HMBPA salts of the present invention include salts prepared via conventional methods from the free acids described herein. An HMBPA salt of the present invention can likewise be converted to a free acid form of 3-(2-hydroxy-3-methyl-butyrylamino)-propionic acid or 3-(2-hydroxy-3-methyl-butyrylamino)-propionate by conventional methodology.

Figure 2:
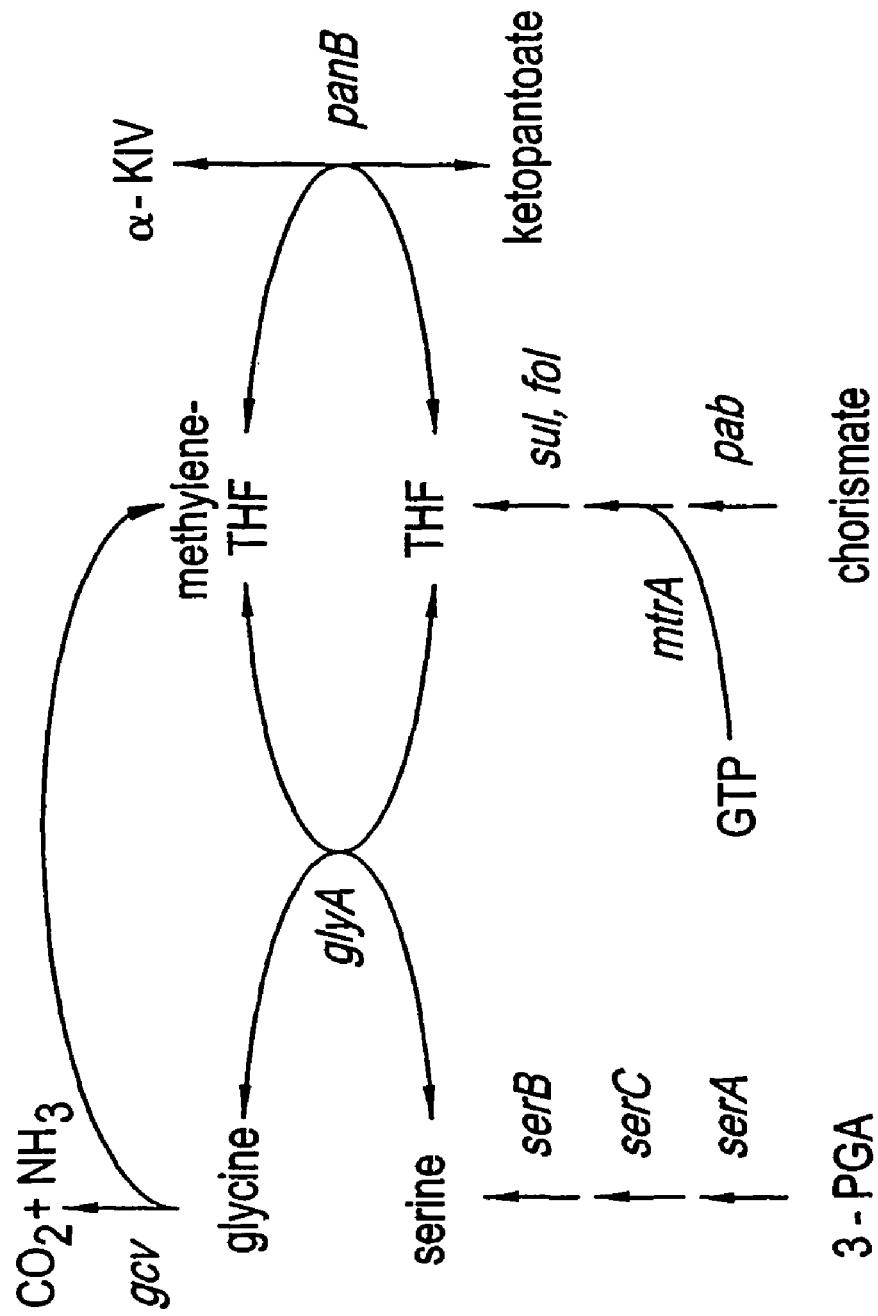
FIG. 2 is a schematic representation of the methylenetetrahydrofolate ("MTF") biosynthetic pathway in *E. coli* (and presumably in *B. subtilis*).

In preferred embodiments, the invention features processes for the enhanced production of panto-compounds (e.g., pantoate and/or pantothenate) that involve culturing a microorganism having a deregulated methylenetetrahydrofolate (MTF) biosynthetic pathway. The term "methylenetetrahydrofolate (MTF) biosynthetic pathway" refers to the biosynthetic pathway involving MTF biosynthetic enzymes (e.g., polypeptides encoded by biosynthetic enzyme-encoding genes), compounds (e.g., substrates, intermediates or products), cofactors and the like utilized in the formation or synthesis of the. PanB substrate, MTF. The term "methylenetetrahydrofolate (MTF) biosynthetic pathway" refers to the biosynthetic pathway leading to the synthesis of MTF in vivo (e.g., the pathway in *E. coli*, as depicted in FIG. 2) as well as the biosynthetic pathway leading to the synthesis of MTF in vitro. The term "methylenetetrahydrofolate (MTF) biosynthetic enzyme" includes any enzyme utilized in the formation of a compound (e.g., intermediate or product) of the methylenetetrahydrofolate (MTF) biosynthetic pathway.

The present invention is based, at least in part, on the discovery that deregulation of certain MTF biosynthetic enzymes results in enhanced production of MTF. A MTF biosynthetic enzyme, the deregulation of which results in enhanced MTF production, is termed a "MTF biosynthesis-enhancing enzyme". Exemplary "MTF biosynthesis-enhancing enzymes" are the serA gene product (3-phosphoglycerate dehydrogenase) and the glyA gene product (serine hydroxymethyl transferase). A microorganism "having a deregulated methylenetetrahydrofolate (MTF) biosynthetic pathway", is a microorganism having at least one MTF biosynthesis-enhancing enzyme deregulated (e.g., overexpressed) such that MTF production or biosynthesis is enhanced (e.g., as compared to MTF production in said microorganism prior to deregulation of said biosynthetic enzyme or as compared to a wild-type microorganism).

In one embodiment, the invention features a process for the enhanced production of panto-compounds (e.g., pantoate and/or pantothenate) that includes culturing a microorganism having a deregulated "methylenetetrahydrofolate (MTF) biosynthetic pathway", as defined herein. In another embodiment, the invention features a process for the enhanced production of panto-compounds (e.g., pantoate and/or pantothenate) that includes culturing a microorganism having a deregulated MTF biosynthesis-enhancing enzyme. In preferred embodiments, the invention features processes for the enhanced production of panto-compounds (e.g., pantoate and/or pantothenate) that includes culturing a microorganism having a deregulated glyA gene product (serine hydroxymethyl transferase) and/or a deregulated serA gene product (3-phosphoglycerate dehydrogenase).

Yet another aspect of the present invention features processes for the enhanced production of pantothenate that include culturing microorganisms under culture conditions selected to favor pantothenate production, for example, by culturing microorganisms with excess serine (a glyA substrate) in the medium. The term "excess serine" includes serine levels increased or higher that those routinely utilized for culturing the microorganism in question. For example, culturing the Bacillus microorganisms described in the instant Examples is routinely done in the presence of about 0-2.5 g/L serine. Accordingly, excess serine levels can include levels of greater than 2.5 g/L serine, for example, between about 2.5 and 10 g/L serine. Excess serine levels can include levels of greater than 5 g/L serine, for example, between about 5 and 10 g/L serine.

Yet another aspect of the invention features further regulating pantothenate kinase activity in pantothenate-producing strains such that pantothenate production is enhanced. Pantothenate kinase is a key enzyme catalyzing the formation of Coenzyme A (CoA) from pantothenate (see e.g., U.S. patent application Ser. No. 09/09/667,569). Regulation of pantothenate kinase (e.g., decreasing the activity or level of pantothenate kinase) reduces the production of CoA, favoring pantothenate accumulation. In one embodiment, pantothenate kinase activity is decreased by deleting CoaA and downregulating CoaX activity (CoaA and CoaX are both capable of catalyzing the first step in CoA biosynthesis in certain microorganisms). In another embodiment, pantothenate kinase activity is decreased by deleting CoaX and downregulating CoaA. In yet another embodiment, pantothenate kinase activity is decreased by downregulating CoaA and CoaX activities.

Yet another aspect of the invention features further regulating pantothenate kinase activity in pantothenate-producing strains such that pantothenate production is enhanced. Pantothenate kinase is a key enzyme catalyzing the formation of Coenzyme A (CoA) from pantothenate (see e.g., U.S. patent application Ser. No. 09/09/667,569). Regulation of pantothenate kinase (e.g., decreasing the activity or level of pantothenate kinase) reduces the production of CoA, favoring pantothenate accumulation. In one embodiment, pantothenate kinase activity is decreased by deleting CoaA and downregulating CoaX activity (CoaA and CoaX are both capable of catalyzing the first step in CoA biosynthesis in certain microorganisms). In another embodiment, pantothenate kinase activity is decreased by deleting CoaX and downregulating CoaA. In yet another embodiment, pantothenate kinase activity is decreased by downregulating CoaA and CoaX activities.

Various aspects of the invention are described in further detail in the following subsections.

I. Targeting Genes Encoding Various Pantothenate and/or Isoleucine-Valine (ilv) and/or Methylenetetrahydrofolate (MTF) Biosynthetic Enzymes In one embodiment, the present invention features modifying or increasing the level of various biosynthetic enzymes of the pantothenate and/or isoleucine-valine(ilv) and/or methylenetetrahydrofolate (MTF) biosynthetic pathways. In particular, the invention features modifying various enzymatic activities associated with said pathways by modifying or altering the genes encoding said biosynthetic enzymes.

The term "gene", as used herein, includes a nucleic acid molecule (e.g., a DNA molecule or segment thereof) that, in an organism, can be separated from another gene or other genes, by intergenic DNA (i.e., intervening or spacer DNA which naturally flanks the gene and/or separates genes in the chromosomal DNA of the organism). Alternatively, a gene may slightly overlap another gene (e.g., the 3' end of a first gene overlapping the 5' end of a second gene), the overlapping genes separated from other genes by intergenic DNA. A gene may direct synthesis of an enzyme or other protein molecule (e.g., may comprise coding sequences, for example, a contiguous open reading frame (ORF) which encodes a protein) or may itself be functional in the organism. A gene in an organism, may be clustered in an operon, as defined herein, said operon being separated from other genes and/or operons by the intergenic DNA. An "isolated gene", as used herein, includes a gene which is essentially free of sequences which naturally flank the gene in the chromosomal DNA of the organism from which the gene is derived (i.e., is free of adjacent coding sequences that encode a second or distinct protein, adjacent structural sequences or the like) and optionally includes 5' and 3' regulatory sequences, for example promoter sequences and/or terminator sequences. In one embodiment, an isolated gene includes predominantly coding sequences for a protein (e.g., sequences which encode Bacillus proteins). In another embodiment, an isolated gene includes coding sequences for a protein (e.g., for a Bacillus protein) and adjacent 5' and/or 3' regulatory sequences from the chromosomal DNA of the organism from which the gene is derived (e.g., adjacent 5' and/or 3' Bacillus regulatory sequences). Preferably, an isolated gene contains less than about 10 kb, 5 kb, 2 kb, 1 kb, 0.5 kb, 0.2 kb, 0.1 kb, 50 bp, 25 bp or 10 bp of nucleotide sequences which naturally flank the gene in the chromosomal DNA of the organism from which the gene is derived.

The term "operon" includes at least two adjacent genes or ORFs, optionally overlapping in sequence at either the 5' or 3' end of at least one gene or ORF. The term "operon" includes a coordinated unit of gene expression that contains a promoter and possibly a regulatory element associated with one or more adjacent genes or ORFs (e.g., structural genes encoding enzymes, for example, biosynthetic enzymes). Expression of the genes (e.g., structural genes) can be coordinately regulated, for example, by regulatory proteins binding to the regulatory element or by anti-termination of transcription. The genes of an operon (e.g., structural genes) can be transcribed to give a single mRNA that encodes all of the proteins.

A "gene having a mutation" or "mutant gene" as used herein, includes a gene having a nucleotide sequence which includes at least one alteration (e.g., substitution, insertion, deletion) such that the polypeptide or protein encoded by said mutant exhibits an activity that differs from the polypeptide or protein encoded by the wild-type nucleic acid molecule or gene. In one embodiment, a gene having a mutation or mutant gene encodes a polypeptide or protein having an increased activity as compared to the polypeptide or protein encoded by the wild-type gene, for example, when assayed under similar conditions (e.g., assayed in microorganisms cultured at the same temperature). As used herein, an "increased activity" or "increased enzymatic activity" is one that is at least 5% greater than that of the polypeptide or protein encoded by the wild-type nucleic acid molecule or gene, preferably at least 5-10% greater, more preferably at least 10-25% greater and even more preferably at least 25-50%, 50-75% or 75-100% greater than that of the polypeptide or protein encoded by the wild-type nucleic acid molecule or gene. Ranges intermediate to the above-recited values, e.g., 75-85%, 85-90%, 90-95%, are also intended to be encompassed by the present invention. As used herein, an "increased activity" or "increased enzymatic activity" can also include an activity that is at least 1.25-fold greater than the activity of the polypeptide or protein encoded by the wild-type gene, preferably at least 1.5-fold greater, more preferably at least 2-fold greater and even more preferably at least 3-fold, 4-fold, 5-fold, 10-fold, 20-fold, 50-fold, 100-fold greater than the activity of the polypeptide or protein encoded by the wild-type gene.

In another embodiment, a gene having a mutation or mutant gene encodes a polypeptide or protein having a reduced activity as compared to the polypeptide or protein encoded by the wild-type gene, for example, when assayed under similar conditions (e.g., assayed in microorganisms cultured at the same temperature). A mutant gene also can encode no polypeptide or have a reduced level of production of the wild-type polypeptide. As used herein, a "reduced activity" or "reduced enzymatic activity" is one that is at least 5% less than that of the polypeptide or protein encoded by the wild-type nucleic acid molecule or gene, preferably at least 5-10% less, more preferably at least 10-25% less and even more preferably at least 25-50%, 50-75% or 75-100% less than that of the polypeptide or protein encoded by the wild-type nucleic acid molecule or gene. Ranges intermediate to the above-recited values, e.g., 75-85%, 85-90%, 90-95%, are also intended to be encompassed by the present invention. As used herein, a "reduced activity" or "reduced enzymatic activity" can also include an activity that has been deleted or "knocked out" (e.g., approximately 100% less activity than that of the polypeptide or protein encoded by the wild-type nucleic acid molecule or gene).

Activity can be determined according to any well accepted assay for measuring activity of a particular protein of interest. Activity can be measured or assayed directly, for example, measuring an activity of a protein in a crude cell extract or isolated or purified from a cell or microorganism. Alternatively, an activity can be measured or assayed within a cell or microorganism or in an extracellular medium. For example, assaying for a mutant gene (i e., said mutant encoding a reduced enzymatic activity) can be accomplished by expressing the mutated gene in a microorganism, for example, a mutant microorganism in which the enzyme is a temperature-sensitive, and assaying the mutant gene for the ability to complement a temperature sensitive (Ts) mutant for enzymatic activity. A mutant gene that encodes an "increased enzymatic activity" can be one that complements the Ts mutant more effectively than, for example, a corresponding wild-type gene. A mutant gene that encodes a "reduced enzymatic activity" is one that complements the Ts mutant less effectively than, for example, a corresponding wild-type gene.

It will be appreciated by the skilled artisan that even a single substitution in a nucleic acid or gene sequence (e.g., a base substitution that encodes an amino acid change in the corresponding amino acid sequence) can dramatically affect the activity of an encoded polypeptide or protein as compared to the corresponding wild-type polypeptide or protein. A mutant gene (e.g., encoding a mutant polypeptide or protein), as defined herein, is readily distinguishable from a nucleic acid or gene encoding a protein homologue in that a mutant gene encodes a protein or polypeptide having an altered activity, optionally observable as a different or distinct phenotype in a microorganism expressing said mutant gene or producing said mutant protein or polypeptide (i.e., a mutant microorganism) as compared to a corresponding microorganism expressing the wild-type gene. By contrast, a protein homologue can have an identical or substantially similar activity, optionally phenotypically undiscernible when produced in a microorganism, as compared to a corresponding microorganism expressing the wild-type gene. Accordingly it is not, for example, the degree of sequence identity between nucleic acid molecules, genes, protein or polypeptides that serves to distinguish between homologues and mutants, rather it is the activity of the encoded protein or polypeptide that distinguishes between homologues and mutants: homologues having, for example, low (e.g., 30-50% sequence identity) sequence identity yet having substantially equivalent functional activities, and mutants, for example sharing 99% sequence identity yet having dramatically different or altered functional activities.

It will also be appreciated by the skilled artisan that nucleic acid molecules, genes, protein or polypeptides for use in the instant invention can be derived from any microorganisms having a MTF biosynthetic pathway, an ilv biosynthetic pathway or a pantothenate biosynthetic pathway. Such nucleic acid molecules, genes, protein or polypeptides can be identified by the skilled artisan using known techniques such as homology screening, sequence comparison and the like, and can be modified by the skilled artisan in such a way that expression or production of these nucleic acid molecules, genes, protein or polypeptides occurs in a recombinant microorganism (e.g., by using appropriate promoters, ribosomal binding sites, expression or integration vectors, modifying the sequence of the genes such that the transcription is increased (taking into account the preferable codon usage), etc., according to techniques described herein and those known in the art).

In one embodiment, the genes of the present invention are derived from a Gram positive microorganism organism (e.g., a microorganism which retains basic dye, for example, crystal violet, due to the presence of a Gram-positive wall surrounding the microorganism). The term "derived from" (e.g., "derived from" a Gram positive microorganism) refers to a gene which is naturally found in the microorganism (e.g., is naturally found in a Gram positive microorganism). In a preferred embodiment, the genes of the present invention are derived from a microorganism belonging to a genus selected from the group consisting of *Bacillus, Cornyebacterium* (e.g., *Cornyebacterium glutamicum*), *Lactobacillus, Lactococci* and *Streptomyces*. In a more preferred embodiment, the genes of the present invention are derived from a microorganism is of the genus *Bacillus*. In another preferred embodiment, the genes of the present invention are derived from a microorganism selected from the group consisting of *Bacillus subtilis, Bacillus lentimorbus, Bacillus lentus, Bacillus firmus, Bacillus pantothenticus, Bacillus amyloliquefaciens, Bacillus cereus, Bacillus circulans, Bacillus coagulans, Bacillus licheniformis, Bacillus megaterium, Bacillus pumilus, Bacillus thuringiensis, Bacillus halodurans*, and other Group 1 *Bacillus* species, for example, as characterized by 16S rRNA type. In another preferred embodiment, the gene is derived from *Bacillus brevis* or *Bacillus stearothermophilus*. In another preferred embodiment, the genes of the present invention are derived from a microorganism selected from the group consisting of *Bacillus licheniformis, Bacillus amyloliquefaciens, Bacillus subtilis*, and *Bacillus pumilus*. In a particularly preferred embodiment, the gene is derived from *Bacillus subtilis* (e.g., is *Bacillus subtilis*-derived). The term "derived from *Bacillus subtilis*" or "*Bacillus subtilis*-derived" includes a gene which is naturally found in the microorganism *Bacillus subtilis*. Included within the scope of the present invention are *Bacillus*-derived genes (e.g., *B. subtilis*-derived genes), for example, *Bacillus* or *B. subtilis* coax genes, serA genes, glyA genes, CoaA genes, pan genes and/or ilv genes.

In another embodiment, the genes of the present invention are derived from a Gram negative (excludes basic dye) microorganism. In a preferred embodiment, the genes of the present invention are derived from a microorganism belonging to a genus selected from the group consisting of Salmonella (e.g., *Salmonella typhimurium*), *Escherichia, Klebsiella, Serratia*, and *Proteus*. In a more preferred embodiment, the genes of the present invention are derived from a microorganism of the genus *Escherichia*. In an even more preferred embodiment, the genes of the present invention are derived from *Escherichia coli*. In another embodiment, the genes of the present invention are derived from *Saccharomyces* (e.g., *Saccharomyces cerevisiae*).

II Recombinant Nucleic Acid Molecules and Vectors

The present invention further features recombinant nucleic acid molecules (e.g., recombinant DNA molecules) that include genes described herein (e.g., isolated genes), preferably *Bacillus* genes, more preferably *Bacillus subtilis* genes, even more preferably *Bacillus subtilis* pantothenate biosynthetic genes and/or isoleucine-valine (ilv) biosynthetic genes and/or methylenetetrahydrofolate (MTF) biosynthetic genes. The term "recombinant nucleic acid molecule" includes a nucleic acid molecule (e.g., a DNA molecule) that has been altered, modified or engineered such that it differs in nucleotide sequence from the native or natural nucleic acid molecule from which the recombinant nucleic acid molecule was derived (e.g., by addition, deletion or substitution of one or more nucleotides). Preferably, a recombinant nucleic acid molecule (e.g., a recombinant DNA molecule) includes an isolated gene of the present invention operably linked to regulatory sequences. The phrase "operably linked to regulatory sequence(s)" means that the nucleotide sequence of the gene of interest is linked to the regulatory sequence(s) in a manner which allows for expression (e.g., enhanced, increased, constitutive, basal, attenuated, decreased or repressed expression) of the gene, preferably expression of a gene product encoded by the gene (e.g., when the recombinant nucleic acid molecule is included in a recombinant vector, as defined herein, and is introduced into a microorganism).

The term "regulatory sequence" includes nucleic acid sequences which affect (e.g., modulate or regulate) expression of other nucleic acid sequences (i.e., genes). In one embodiment, a regulatory sequence is included in a recombinant nucleic acid molecule in a similar or identical position and/or orientation relative to a particular gene of interest as is observed for the regulatory sequence and gene of interest as it appears in nature, e.g., in a native position and/or orientation. For example, a gene of interest can be included in a recombinant nucleic acid molecule operably linked to a regulatory sequence which accompanies or is adjacent to the gene of interest in the natural organism (e.g., operably linked to "native" regulatory sequences (e.g., to the "native" promoter). Alternatively, a gene of interest can be included in a recombinant nucleic acid molecule operably linked to a regulatory sequence which accompanies or is adjacent to another (e.g., a different) gene in the natural organism. Alternatively, a gene of interest can be included in a recombinant nucleic acid molecule operably linked to a regulatory sequence from another organism. For example, regulatory sequences from other microbes (e.g., other bacterial regulatory sequences, bacteriophage regulatory sequences and the like) can be operably linked to a particular gene of interest.

In one embodiment, a regulatory sequence is a non-native or non-naturally-occurring sequence (e.g., a sequence which has been modified, mutated, substituted, derivatized, deleted including sequences which are chemically synthesized). Preferred regulatory sequences include promoters, enhancers, termination signals, anti-termination signals and other expression control elements (e.g., sequences to which repressors or inducers bind and/or binding sites for transcriptional and/or translational regulatory proteins, for example, in the transcribed mRNA). Such regulatory sequences are described, for example, in Sambrook, J., Fritsh, E. F., and Maniatis, T. *Molecular Cloning: A Laboratory Manual. 2nd, ed, Cold Spring Harbor Laboratory*, Cold Spring Harbor Laboratory Press, Cold Spring Harbor, N.Y., 1989. Regulatory sequences include those which direct constitutive expression of a nucleotide sequence in a microorganism (e.g., constitutive promoters and strong constitutive promoters), those which direct inducible expression of a nucleotide sequence in a microorganism (e.g., inducible promoters, for example, xylose inducible promoters) and those which attenuate or repress expression of a nucleotide sequence in a microorganism (e.g., attenuation signals or repressor sequences). It is also within the scope of the present invention to regulate expression of a gene of interest by removing or deleting regulatory sequences. For example, sequences involved in the negative regulation of transcription can be removed such that expression of a gene of interest is enhanced.

In one embodiment, a recombinant nucleic acid molecule of the present invention includes a nucleic acid sequence or gene that encodes at least one bacterial gene product (e.g., a pantothenate biosynthetic enzyme, an isoleucine-valine biosynthetic enzyme and/or a methylenetetrahydrofolate (MTF) biosynthetic enzyme) operably linked to a promoter or promoter sequence. Preferred promoters of the present invention include *Bacillus* promoters and/or bacteriophage promoters (e.g., bacteriophage which infect *Bacillus*). In one embodiment, a promoter is a *Bacillus* promoter, preferably a strong *Bacillus* promoter (e.g., a promoter associated with a biochemical housekeeping gene in *Bacillus* or a promoter associated with a glycolytic pathway gene in *Bacillus*). In another embodiment, a promoter is a bacteriophage promoter. In a preferred embodiment, the promoter is from the bacteriophage SP01. In a particularly preferred embodiment, a promoter is selected from the group consisting of $P_{15}$, $P_{26}$ or $P_{veg}$, having for example, the following respective seqeunces:

GCTATTGACGACAGCTATGGTTCACT-
GTCCACCAACCAAAACTGTGCTCAGTA CCGC-
CAATATTTCTCCCTTGAGGGGTACAAA-
GAGGTGTCCCTAGAAGAGATC
CACGCTGTGTAAAAATTTTACAAAAAGG-
TATTGACTTTCCCTACAGGGTGTGT AATAATT-
TAATTACAGGCGGGGGCAACCCCGCCTGT(SEQ
ID NO:1), GCCTACCTAGCTTCCAAGAAAGATATC-
CTAACAGCACAAGAGCGGAAAGATG TTTTGTTC-
TACATCCAGAACAACCTCTGCTAAAAT-
TCCTGAAAAATTTTGCAA
AAAGTTGTTGACTTTATCTACAAGGT-
GTGGTATAATAATCTTAACAACAGCAG GACGC
(SEQ ID NO:2), and
GAGGAATCATAGAATTTTGT-
CAAAATAATTTTATTGACAACGTCTTATTAACG
TTGATATAATTTAAATTTTATTTGA-
CAAAAATGGGCTCGTGTTGTACAATAAA
TGTAGTGAGGTGGATGCAATG (SEQ ID NO:3).
Additional preferred promoters include tef (the translational elongation factor (TEF) promoter) and pyc (the pyruvate carboxylase (PYC) promoter), which promote high level expression in *Bacillus* (e.g., *Bacillus subtilis*). Additional preferred promoters, for example, for use in Gram positive microorganisms include, but are not limited to, amy and SPO2 promoters. Additional preferred promoters, for example, for use in Gram negative microorganisms include, but are not limited to, cos, tac, trp, tet, trp-tet, lpp, lac, lpp-lac, lacIQ, T7, T5, T3, gal, trc, ara, SP6, λ-PR or λ-PL.

In another embodiment, a recombinant nucleic acid molecule of the present invention includes a terminator sequence or terminator sequences (e.g., transcription terminator sequences). The term "terminator sequences" includes regulatory sequences that serve to terminate transcription of mRNA. Terminator sequences (or tandem transcription terminators) can further serve to stabilize mRNA (e.g., by adding structure to mRNA), for example, against nucleases.

In yet another embodiment, a recombinant nucleic acid molecule of the present invention includes sequences that allow for detection of the vector containing said sequences (i.e., detectable and/or selectable markers), for example, genes that encode antibiotic resistance sequences or that overcome auxotrophic mutations, for example, trpC, drug markers, fluorescent markers, and/or calorimetric markers (e.g., lacZ/β-galactosidase). In yet another embodiment, a recombinant nucleic acid molecule of the present invention includes an artificial ribosome binding site (RBS) or a sequence that gets transcribed into an artificial RBS. The term "artificial ribosome binding site (RBS)" includes a site within an mRNA molecule (e.g., coded within DNA) to which a ribosome binds (e.g., to initiate translation) which differs from a native RBS (e.g., a RBS found in a naturally-occurring gene) by at least one nucleotide. Preferred artificial RBSs include about 5-6,7-8, 9-10, 11-12, 13-14, 15-16, 17-18, 19-20, 21-22, 23-24, 25-26, 27-28, 29-30 or more nucleotides of which about 1-2, 34, 5-6,7-8, 9-10, 11-12, 13-15 or more differ from the native RBS (e.g., the native RBS of a gene of interest, for example, the native panB RBS TAAACATGAGGAGGAGAAAACATG (SEQ ID NO:4) or the native panD RBS ATTCGAGAAATG-GAGAGAATATAATATG (SEQ ID NO:5)). Preferably, nucleotides that differ are substituted such that they are identical to one or more nucleotides of an ideal RBS when optimally aligned for comparisons. Ideal RBSs include, but are not limited to, AGAAAGGAGGTGA (SEQ ID NO:6), TTAAGAAAGGAGGTGANNNNATG (SEQ ID NO:7), TTAGAAAGGAGGTGANNNNNATG (SEQ ID NO:8), AGAAAGGAGGTGANNNNNNATG (SEQ ID NO:9), and AGAAAGGAGGTGANNNNNNNATG (SEQ ID NO:10). Artificial RBSs can be used to replace the naturally-occurring or native RBSs associated with a particular gene. Artificial RBSs preferably increase translation of a particular gene. Preferred artificial RBSs (e.g., RBSs for increasing the translation of panB, for example, of *B. subtilis* panB) include CCCTCTAGAAGGAG-GAGAAAACATG (SEQ ID NO:11) and CCCTCTA-GAGGAGGAGAAAACATG (SEQ ID NO:12). Preferred artificial RBSs (e.g., RBSs for increasing the translation of panD, for example, of *B. subtilis* panD) include TTAGAAAGGAGGATTTAAATATG (SEQ ID NO:13),
TTAGAAAGGAGGTTTAATTAATG (SEQ ID NO:14),
TTAGAAAGGAGGTGATTTAAATG (SEQ ID NO:15),
TTAGAAAGGAGGTGTTTAAAATG (SEQ ID NO:16),
ATTCGAGAAAGGAGG TGAATATAATATG (SEQ ID NO:17), ATTCGAGAAAGGAGGTGAATAATAATG (SEQ ID NO:18), and ATTCGTAGAAAGGAGGT-GAATTAATATG (SEQ ID NO:19).

The present invention further features vectors (e.g., recombinant vectors) that include nucleic acid molecules (e.g., genes or recombinant nucleic acid molecules comprising said genes) as described herein. The term "recombinant vector" includes a vector (e.g., plasmid, phage, phasmid, virus, cosmid or other purified nucleic acid vector) that has been altered, modified or engineered such that it contains greater, fewer or different nucleic acid sequences than those included in the native or natural nucleic acid molecule from which the recombinant vector was derived. Preferably, the recombinant vector includes a biosynthetic enzyme-encoding gene or recombinant nucleic acid molecule including said gene, operably linked to regulatory sequences, for example, promoter sequences, terminator sequences and/or artificial ribosome binding sites (RBSs), as defined herein. In another embodiment, a recombinant vector of the present invention includes sequences that enhance replication in bacteria (e.g., replication-enhancing sequences). In one embodiment, replication-enhancing sequences function in *E. coli*. In another embodiment, replication-enhancing sequences are derived from pBR322.

In yet another embodiment, a recombinant vector of the present invention includes antibiotic resistance sequences. The term "antibiotic resistance sequences" includes sequences which promote or confer resistance to antibiotics on the host organism (e.g., *Bacillus*). In one embodiment, the antibiotic resistance sequences are selected from the group consisting of cat (chloramphenicol resistance) sequences, tet (tetracycline resistance) sequences, erm (erythromycin resistance) sequences, neo (neomycin resistance) sequences, kan (kanamycin resistance) sequences and spec (spectinomycin resistance) sequences. Recombinant vectors of the present invention can further include homologous recombination sequences (e.g., sequences designed to allow recombination of the gene of interest into the chromosome of the host organism). For example, bpr, vpr, or amyE sequences can be used as homology targets for recombination into the host chromosome. It will further be appreciated by one of skill in the art that the design of a vector can be tailored depending on such factors as the choice of microorganism to be genetically engineered, the level of expression of gene product desired and the like.

IV. Recombinant Microorganisms

The present invention further features microorganisms, i.e., recombinant microorganisms, that include vectors or genes (e.g., wild-type and/or mutated genes) as described herein. As used herein, the term "recombinant microorganism" includes a microorganism (e.g., bacteria, yeast cell, fungal cell, etc.) that has been genetically altered, modified or engineered (e.g., genetically engineered) such that it exhibits an altered, modified or different genotype and/or phenotype (e.g., when the genetic modification affects coding nucleic acid sequences of the microorganism) as compared to the naturally-occurring microorganism from which it was derived.

In one embodiment, a recombinant microorganism of the present invention is a Gram positive organism (e.g., a microorganism which retains basic dye, for example, crystal violet, due to the presence of a Gram-positive wall surrounding the microorganism). In a preferred embodiment, the recombinant microorganism is a microorganism belonging to a genus selected from the group consisting of *Bacillus, Cornyebacterium* (e.g., *Cornyebacterium glutamicum*), *Lactobacillus, Lactococci* and *Streptomyces*. In a more preferred embodiment, the recombinant microorganism is of the genus *Bacillus*. In another preferred embodiment, the recombinant microorganism is selected from the group consisting of *Bacillus subtilis, Bacillus lentimorbus, Bacillus lentus, Bacillus firmus, Bacillus pantothenticus, Bacillis amyloliquefaciens, Bacillus cereus, Bacillus circulans, Bacillus coagulans, Bacillus licheniformis, Bacillus megaterium, Bacillus pumilus, Bacillus thuringiensis, Bacillus halodurans*, and other Group 1 *Bacillus* species, for example, as characterized by 16S rRNA type. In another preferred embodiment, the recombinant microorganism is *Bacillus brevis* or *Bacillus stearothermophilus*. In another preferred embodiment, the recombinant microorganism is selected from the group consisting of *Bacillus licheniformis, Bacillus amyloliquefaciens, Bacillus subtilis*, and *Bacillus pumilus*.

In another embodiment, the recombinant microorganism is a Gram negative (excludes basic dye) organism. In a preferred embodiment, the recombinant microorganism is a microorganism belonging to a genus selected from the group consisting of Salmonella (e.g., *Salmonella typhimurium*), *Escherichia, Klebsiella, Serratia*, and *Proteus*. In a more preferred embodiment, the recombinant microorganism is of the genus *Escherichia*. In an even more preferred embodiment, the recombinant microorganism is *Escherichia coli*. In another embodiment, the recombinant microorganism is *Saccharomyces* (e.g., *Saccharomyces cerevisiae*).

A preferred "recombinant" microorganism of the present invention is a microorganism having a deregulated pantothenate biosynthesis pathway or enzyme, a deregulated isoleucine-valine (ilv) biosynthetic pathway or enzyme and/or a modified or deregulated methylenetetrahydrofolate (MTF) biosynthetic pathway or enzyme. The term "deregulated" or "deregulation" includes the alteration or modification of at least one gene in a microorganism that encodes an enzyme in a biosynthetic pathway, such that the level or activity of the biosynthetic enzyme in the microorganism is altered or modified. Preferably, at least one gene that encodes an enzyme in a biosynthetic pathway is altered or modified such that the gene product is enhanced or increased. The phrase "deregulated pathway" can also include a biosynthetic pathway in which more than one gene that encodes an enzyme in a biosynthetic pathway is altered or modified such that the level or activity of more than one biosynthetic enzyme is altered or modified. The ability to "deregulate" a pathway (e.g., to simultaneously deregulate more than one gene in a given biosynthetic pathway) in a microorganism in some cases arises from the particular phenomenon of microorganisms in which more than one enzyme (e.g., two or three biosynthetic enzymes) are encoded by genes occurring adjacent to one another on a contiguous piece of genetic material termed an "operon" (defined herein). Due to the coordinated regulation of genes included in an operon, alteration or modification of the single promoter and/or regulatory element can result in alteration or modification of the expression of each gene product encoded by the operon. Alteration or modification of the regulatory element can include, but is not limited to removing the endogenous promoter and/or regulatory element(s), adding strong promoters, inducible promoters or multiple promoters or removing regulatory sequences such that expression of the gene products is modified, modifying the chromosomal location of the operon, altering nucleic acid sequences adjacent to the operon or within the operon such as a ribosome binding site, increasing the copy number of the operon. modifying proteins (e.g., regulatory proteins, suppressors, enhancers, transcriptional activators and the like) involved in transcription of the operon and/or translation of the gene products of the operon, or any other conventional means of deregulating expression of genes routine in the art (including but not limited to use of antisense nucleic acid molecules, for example, to block expression of repressor proteins). Deregulation can also involve altering the coding region of one or more genes to yield, for example, an enzyme that is feedback resistant or has a higher or lower specific activity.

In another preferred embodiment, a recombinant microorganism is designed or engineered such that at least one pantothenate biosynthetic enzyme, at least one isoleucine-valine biosynthetic enzyme, and/or at least one MTF biosynthetic enzyme is overexpressed. The term "overexpressed" or "overexpression" includes expression of a gene product (e.g., a biosynthetic enzyme) at a level greater than that expressed prior to manipulation of the microorganism or in a comparable microorganism which has not been manipulated. In one embodiment, the microorganism can be genetically designed or engineered to overexpress a level of gene product greater than that expressed in a comparable microorganism which has not been engineered.

Genetic engineering can include, but is not limited to, altering or modifying regulatory sequences or sites associated with expression of a particular gene (e.g., by adding strong promoters, inducible promoters or multiple promoters or by removing regulatory sequences such that expression is constitutive), modifying the chromosomal location of a particular gene, altering nucleic acid sequences adjacent to a particular gene such as a ribosome binding site, increasing the copy number of a particular gene, modifying proteins (e.g., regulatory proteins, suppressors, enhancers, transcriptional activators and the like) involved in transcription of a particular gene and/or translation of a particular gene product, or any other conventional means of deregulating expression of a particular gene routine in the art (including but not limited to use of antisense nucleic acid molecules, for example, to block expression of repressor proteins). Genetic engineering can also include deletion of a gene, for example, to block a pathway or to remove a repressor.

In another embodiment, the microorganism can be physically or environmentally manipulated to overexpress a level of gene product greater than that expressed prior to manipulation of the microorganism or in a comparable microorganism which has not been manipulated. For example, a microorganism can be treated with or cultured in the presence of an agent known or suspected to increase transcription of a particular gene and/or translation of a particular gene product such that transcription and/or translation are enhanced or increased. Alternatively, a microorganism can be cultured at a temperature selected to increase transcription of a particular gene and/or translation of a particular gene product such that transcription and/or translation are enhanced or increased.

V. Culturing and Fermenting Recombinant Microorganisms

The term "culturing" includes maintaining and/or growing a living microorganism of the present invention (e.g., maintaining and/or growing a culture or strain). In one embodiment, a microorganism of the invention is cultured in liquid media. In another embodiment, a microorganism of the invention is cultured in solid media or semi-solid media. In a preferred embodiment, a microorganism of the invention is cultured in media (e.g., a sterile, liquid medium) comprising nutrients essential or beneficial to the maintenance and/or growth of the microorganism (e.g., carbon sources or carbon substrate, for example carbohydrate, hydrocarbons, oils, fats, fatty acids, organic acids, and alcohols; nitrogen sources, for example, peptone, yeast extracts, meat extracts, malt extracts, soy meal, soy flour, soy grits, urea, ammonium sulfate, ammonium chloride, ammonium nitrate and ammonium phosphate; phosphorus sources, for example, phosphoric acid, sodium and potassium salts thereof; trace elements, for example, magnesium, iron, manganese, calcium, copper, zinc, boron, molybdenum, and/or cobalt salts; as well as growth factors such as amino acids, vitamins, growth promoters and the like).

Preferably, microorganisms of the present invention are cultured under controlled pH. The term "controlled pH" includes any pH which results in production of the desired product (e.g., pantoate and/or pantothenate). In one embodiment microorganisms are cultured at a pH of about 7. In another embodiment, microorganisms are cultured at a pH of between 6.0 and 8.5. The desired pH may be maintained by any number of methods known to those skilled in the art.

Also preferably, microorganisms of the present invention are cultured under controlled aeration. The term "controlled aeration" includes sufficient aeration (e.g., oxygen) to result in production of the desired product (e.g., pantoate and/or pantothenate). In one embodiment, aeration is controlled by regulating oxygen levels in the culture, for example, by regulating the amount of oxygen dissolved in culture media. Preferably, aeration of the culture is controlled by agitating the culture. Agitation may be provided by a propeller or similar mechanical agitation equipment, by revolving or shaking the culture vessel (e.g., tube or flask) or by various pumping equipment. Aeration may be further controlled by the passage of sterile air or oxygen through the medium (e.g., through the fermentation mixture). Also preferably, microorganisms of the present invention are cultured without excess foaming (e.g., via addition of antifoaming agents).

Moreover, microorganisms of the present invention can be cultured under controlled temperatures. The term "controlled temperature" includes any temperature which results in production of the desired product (e.g., pantoate and/or pantothenate). In one embodiment, controlled temperatures include temperatures between 15° C. and 95° C. In another embodiment, controlled temperatures include temperatures between 15° C. and 70° C. Preferred temperatures are between 20° C. and 55° C., more preferably between 30° C. and 50° C.

Microorganisms can be cultured (e.g., maintained and/or grown) in liquid media and preferably are cultured, either continuously or intermittently, by conventional culturing methods such as standing culture, test tube culture, shaking culture (e.g., rotary shaking culture, shake flask culture, etc.), aeration spinner culture, or fermentation. In a preferred embodiment, the microorganisms are cultured in shake flasks. In a more preferred embodiment, the microorganisms are cultured in a fermentor (e.g., a fermentation process). Fermentation processes of the present invention include, but are not limited to, batch, fed-batch and continuous processes or methods of fermentation. The phrase "batch process" or "batch fermentation" refers to a system in which the composition of media, nutrients, supplemental additives and the like is set at the beginning of the fermentation and not subject to alteration during the fermentation, however, attempts may be made to control such factors as pH and oxygen concentration to prevent excess media acidification and/or microorganism death. The phrase "fed-batch process" or "fed-batch" fermentation refers to a batch fermentation with the exception that one or more substrates or supplements are added (e.g., added in increments or continuously) as the fermentation progresses. The phrase "continuous process" or "continuous fermentation" refers to a system in which a defined fermentation media is added continuously to a fermentor and an equal amount of used or "conditioned" media is simultaneously removed, preferably for recovery of the desired product (e.g., pantoate and/or pantothenate). A variety of such processes have been developed and are well-known in the art.

The phrase "culturing under conditions such that a desired compound is produced" includes maintaining and/or growing microorganisms under conditions (e.g., temperature, pressure, pH, duration, etc.) appropriate or sufficient to obtain production of the desired compound or to obtain desired yields of the particular compound being produced. For example, culturing is continued for a time sufficient to produce the desired amount of a compound (e.g., pantoate and/or pantothenate). Preferably, culturing is continued for a time sufficient to substantially reach suitable production of the compound (e.g., a time sufficient to reach a suitable concentration of pantoate and/or pantothenate or suitable ratio of pantoate and/or pantothenate:HMBPA). In one embodiment, culturing is continued for about 12 to 24 hours. In another embodiment, culturing is continued for about 24 to 36 hours, 36 to 48 hours, 48 to 72 hours, 72 to 96 hours, 96 to 120 hours, 120 to 144 hours, or greater than 144 hours. In yet another embodiment, microorganisms are cultured under conditions such that at least about 5 to 10 g/L of compound are produced in about 36 hours, at least about 10 to 20 g/L compound are produced in about 48 hours, or at least about 20 to 30 g/L compound in about 72 hours. In yet another embodiment, microorganisms are cultured under conditions such that at least about 5 to 20 g/L of compound are produced in about 36 hours, at least about 20 to 30 g/L compound are produced in about 48 hours, or at least about 30 to 50 or 60 g/L compound in about 72 hours. In yet another embodiment, microorganisms are cultured under conditions such that at least about 40 to 60 g/L of compound are produced in about 36 hours, or at least about 60 to 90 g/L compound are produced in about 48 hours. It will be appreciated by the skilled artisan that values above the upper limits of the ranges recited may be obtainable by the processes described herein, for example, in a particular fermentation run or with a particular engineered strain.

Preferably, a production method of the present invention results in production of a level of pantothenate that is "enhanced as compared to an appropriate control". The term "appropriate control", as defined herein, includes any control recognized by the skilled artisan as being appropriate for determining enhanced, increased, or elevated levels of desired product. For example, where the process features culturing a microorganism having a deregulated pantothenate biosynthetic pathway and said microorganism further has a deregulated MTF biosynthetic pathway (i.e., has been engineered such that at least one MTF biosynthetic enzyme is deregulated, for example, overexpressed) an appropriate control includes a culture of the microorganism before or absent manipulation of the MTF enzyme or pathway (i.e., having only the pantothenate biosynthetic pathway deregulated). Likewise, where the process features culturing a microorganism having a deregulated pantothenate biosynthetic pathway and a deregulated ilv biosynthetic pathway and said microorganism further has a deregulated MTF biosynthetic pathway (i.e., has been engineered such that at least one MTF biosynthetic enzyme is deregulated, for example, overexpressed) an appropriate control includes a culture of the microorganism before or absent manipulation of the MTF enzyme or pathway (i.e., having only the pantothenate biosynthetic pathway and ilv biosynthetic pathway deregulated). Comparison need not be performed in each process practiced according to the present invention. For example, a skilled artisan can determine appropriate controls empirically from performing a series of reactions (e.g., test tube cultures, shake flask cultures, fermentations), for example, under the same or similar conditions. Having appreciated a routine production level, for example, by a particular strain, the artisan is able to recognize levels that are enhanced, increased or elevated over such levels. In other words, comparison to an appropriate control includes comparison to a predetermined values (e.g., a predetermined control).

Thus, in an embodiment wherein an appropriately engineered strain produces 40 g/L pantothenate in 36 hours (prior to manipulation such that pantothenate production is enhanced), production of 50, 60, 70 or more g/L pantothenate (after manipulation, for example, manipulation such that at least one MTF biosynthetic enzyme is overexpressed) exemplifies enhanced production. Likewise, in an embodiment wherein an appropriately engineered strain produces 50 g/L pantothenate in 48 hours (prior to manipulation such that pantothenate production is enhanced), production of 60, 70, 80, 90 or more g/L pantothenate (after manipulation, for example, manipulation such that at least one MTF biosynthetic enzyme is overexpressed) exemplifies enhanced production.

The methodology of the present invention can further include a step of recovering a desired compound (e.g., pantoate and/or pantothenate). The term "recovering" a desired compound includes extracting, harvesting, isolating or purifying the compound from culture media. Recovering the compound can be performed according to any conventional isolation or purification methodology known in the art including, but not limited to, treatment with a conventional resin (e.g., anion or cation exchange resin, non-ionic adsorption resin, etc.), treatment with a conventional adsorbent (e.g., activated charcoal, silicic acid, silica gel, cellulose, alumina, etc.), alteration of pH, solvent extraction (e.g., with a conventional solvent such as an alcohol, ethyl acetate, hexane and the like), dialysis, filtration, concentration, crystallization, recrystallization, pH adjustment, lyophilization and the like. For example, a compound can be recovered from culture media by first removing the microorganisms from the culture. Media are then passed through or over a cation exchange resin to remove cations and then through or over an anion exchange resin to remove inorganic anions and organic acids having stronger acidities than the compound of interest. The resulting compound can subsequently be converted to a salt (e.g., a calcium salt) as described herein.

Preferably, a desired compound of the present invention is "extracted", "isolated" or "purified" such that the resulting preparation is substantially free of other media components (e.g., free of media components and/or fermentation byproducts). The language "substantially free of other media components" includes preparations of the desired compound in which the compound is separated from media components or fermentation byproducts of the culture from which it is produced. In one embodiment, the preparation has greater than about 80% (by dry weight) of the desired compound (e.g., less than about 20% of other media components or fermentation byproducts), more preferably greater than about 90% of the desired compound (e.g., less than about 10% of other media components or fermentation byproducts), still more preferably greater than about 95% of the desired compound (e.g., less than about 5% of other media components or fermentation byproducts), and most preferably greater than about 98-99% desired compound (e.g., less than about 1-2% other media components or fermentation byproducts). When the desired compound has been derivatized to a salt, the compound is preferably further free of chemical contaminants associated with the formation of the salt. When the desired compound has been derivatized to an alcohol, the compound is preferably further free of chemical contaminants associated with the formation of the alcohol.

In an alternative embodiment, the desired compound is not purified from the microorganism, for example, when the microorganism is biologically non-hazardous (e.g., safe). For example, the entire culture (or culture supernatant) can be used as a source of product (e.g., crude product). In one embodiment, the culture (or culture supernatant) is used without modification. In another embodiment, the culture (or culture supernatant) is concentrated. In yet another embodiment, the culture (or culture supernatant) is dried or lyophilized.

In yet another embodiment, the desired compound is partially purified. The term "partially purified" includes media preparations that have had at least some processing, for example, treatment (e.g., batch treatment) with a commercial resin. In preferred embodiments, the "partially purified" preparation has greater than about 30% (by dry weight) of the desired compound, preferably greater than about 40% of the desired compound, more preferably greater than about 50% of the desired compound, still more preferably greater than about 60% of the desired compound, and most preferably greater than about 70% desired compound. "Partially purified" preparations also preferably have 80% or less (by dry weight) of the desired compound (i.e., are less pure than "extracted", "isolated" or "purified" preparations, as defined herein).

Depending on the biosynthetic enzyme or combination of biosynthetic enzymes manipulated, it may be desirable or necessary to provide (e.g., feed) microorganisms of the present invention at least one biosynthetic precursor such that the desired compound or compounds are produced. The term "biosynthetic precursor" or "precursor" includes an agent or compound which, when provided to, brought into contact with, or included in the culture medium of a microorganism, serves to enhance or increase biosynthesis of the desired product. In one embodiment, the biosynthetic precursor or precursor is aspartate. In another embodiment, the biosynthetic precursor or precursor is β-alanine. The amount of aspartate or β-alanine added is preferably an amount that results in a concentration in the culture medium sufficient to enhance productivity of the microorganism (e.g., a concentration sufficient to enhance production of pantoate and/or pantothenate). Biosynthetic precursors of the present invention can be added in the form of a concentrated solution or suspension (e.g., in a suitable solvent such as water or buffer) or in the form of a solid (e.g., in the form of a powder). Moreover, biosynthetic precursors of the present invention can be added as a single aliquot, continuously or intermittently over a given period of time. The term "excess β-alanine" includes β-alanine levels increased or higher that those routinely utilized for culturing the microorganism in question. For example, culturing the Bacillus microorganisms described in the instant Examples is routinely done in the presence of about 0-0.01 g/L β-alanine. Accordingly, excess β-alanine levels can include levels of about 0.01-1, preferably about 1-20 g/L.

In yet another embodiment, the biosynthetic precursor is valine. In yet another embodiment, the biosynthetic precursor is α-ketoisovalerate. Preferably, valine or α-ketoisovalerate is added in an amount that results in a concentration in the medium sufficient for production of the desired product (e.g., pantoate and/or pantothenate) to occur. The term "excess α-KIV" includes α-KIV levels increased or higher that those routinely utilized for culturing the microorganism in question. For example, culturing the Bacillus microorganisms described in the instant Examples is routinely done in the presence of about 0-0.01 g/L α-KIV. Accordingly, excess α-KIV levels can include levels of about 0.01-1, preferably about 1-20 g/L α-KIV. The term "excess valine" includes valine levels increased or higher that those routinely utilized for culturing the microorganism in question. For example, culturing the Bacillus microorganisms described in the instant Examples is routinely done in the presence of about 0-0.5 g/L valine. Accordingly, excess valine levels can include levels of about 0.5-5 g/L, preferably about 5-20 g/L valine.

In yet another embodiment, the biosynthetic precursor is serine. Preferably, serine is added in an amount that results in a concentration in the medium sufficient for production of the desired product (e.g., pantoate and/or pantothenate) to occur. Excess serine (as defined herein) can also be added according to the production processes described herein, for example, for the enhanced production of pantothenate. The skilled artisan will appreciate that extreme excesses of biosynthetic precursors can result in microorganism toxicity. Biosynthetic precursors are also referred to herein as "supplemental biosynthetic substrates".

Another aspect of the present invention includes biotransformation processes which feature the recombinant microorganisms described herein. The term "biotransformation process", also referred to herein as "bioconversion processes", includes biological processes which results in the production (e.g., transformation or conversion) of appropriate substrates and/or intermediate compounds into a desired product.

The microorganism(s) and/or enzymes used in the biotransformation reactions are in a form allowing them to perform their intended function (e.g., producing a desired compound). The microorganisms can be whole cells, or can be only those portions of the cells necessary to obtain the desired end result. The microorganisms can be suspended (e.g., in an appropriate solution such as buffered solutions or media), rinsed (e.g., rinsed free of media from culturing the microorganism), acetone-dried, immobilized (e.g., with polyacrylamide gel or k-carrageenan or on synthetic supports, for example, beads, matrices and the like), fixed, cross-linked or permeablized (e.g., have permeablized membranes and/or walls such that compounds, for example, substrates, intermediates or products can more easily pass through said membrane or wall).

This invention is further illustrated by the following examples which should not be construed as limiting. The contents of all references, patents and published patent applications cited throughout this application are incorporated herein by reference.

EXAMPLES

Example I

Panto-Compound Production Strains

In developing Bacillus strains for the production of pantothenate, various genetic manipulations are made to genes and enzymes involved in the pantothenate biosynthetic pathway and the isoleucine-valine (ilv) pathway (FIG. 1) as described in U.S. patent application Ser. No. 09/400,494 and U.S. patent application Ser. No. 09/667,569. For example, strains having a deregulated panBCD operon and/or having deregulated panE1 exhibit enhanced pantothenate production (when cultured in the presence of β-alanine and α-ketoisovalerate (α-KIV)). Strains further deregulated for ilvBNC and ilvD exhibit enhanced pantothenate production in the presence of only β-alanine. Moreover, it is possible to achieve β-alanine independence by further deregulating panD.

An exemplary pantothenate production strain is PA824, a tryptophan prototroph, Spec and Tet resistant, deregulated for panBCD at the panBCD locus, deregulated for panE1 at the panE1 locus (two genes in the B. subtilis genome are homologous to E. coli panE, panE1 and panE2, the former encoding the major ketopantoate reductase involved in pantothenate production, while panE2 does not contribute to pantothenate synthesis (U.S. patent application Ser. No. 09/400,494), deregulated for ilvD at the ilvD locus, overexpressing an ilvBNC cassette at the amyE locus, and overexpressing panD at the bpr locus. PA824 routinely yields approximately 40-50 g/L pantothenate, when cultured for 48 hours in 14 L fermentor vessels according to standard fermentation procedures (see e.g., provisional Patent Application Ser. No. 60/263,053 or provisional Patent Application Ser. No. 60/262,995, incorporated by reference herein). Briefly, batch media (4.5 L) containing trace elements is inoculated with shake flask cultures of PA824. The fermentations are controlled for temperature (e.g., 43° C.), dissolved $O_2$, and pH, and are run as a glucose limited fed batch process. After the initial batched glucose is consumed, glucose concentrations are maintained between about 0 and 1 g/L by continuous feeding of fresh FEED media. pH is set at 7.2, monitored, and maintained by feeding either a NH$_3$—or a H$_3$PO$_4$-solution. The dissolved oxygen concentration [pO$_2$] is maintained at about 10-30% by regulation of the agitation and aeration rate. Foaming is controlled by addition of an appropriate antifoam agent. The pantothenate titer in the fermentation broth is determined (by HPLC analysis) after removal of the cells by centrifugation.

A second exemplary strain is PA668. PA668 is a derivative of PA824 that contains extra copies of P$_{26}$ panB amplified at the vpr and/or panB locus. PA668 was constructed using a panB expression vector (pAN636) which allows for selection of multiple copies using chloramphenicol. Briefly, a pAN636 NotI restriction fragment (excluding vector sequences) was ligated and then used to transform PA824 with selection on plates containing 5 μg/ml chloramphenicol. Transformants resistant to 30 μg/ml chloramphenicol were isolated and screened for pantothenate production in 48 hour test tube cultures. The isolates produce about 10 percent more pantothenate than PA824. In 10-L fermentations, a first strain, PA668-2A, produces pantothenate in amounts comparable to PA824 cultured under similar conditions (e.g., ~45-50 g/L at 36 hours). After 36 hours, when pantothenate production routinely begins to slow with PA824, PA668-2A continues to produce significant levels of pantothenate (e.g., ~60-65 g/l pantothenate at 48 hours). A second strain, PA668-24, produces pantothenate at an even faster rate, reaching 60-70 g/L after 48 hours.

Figure 4:
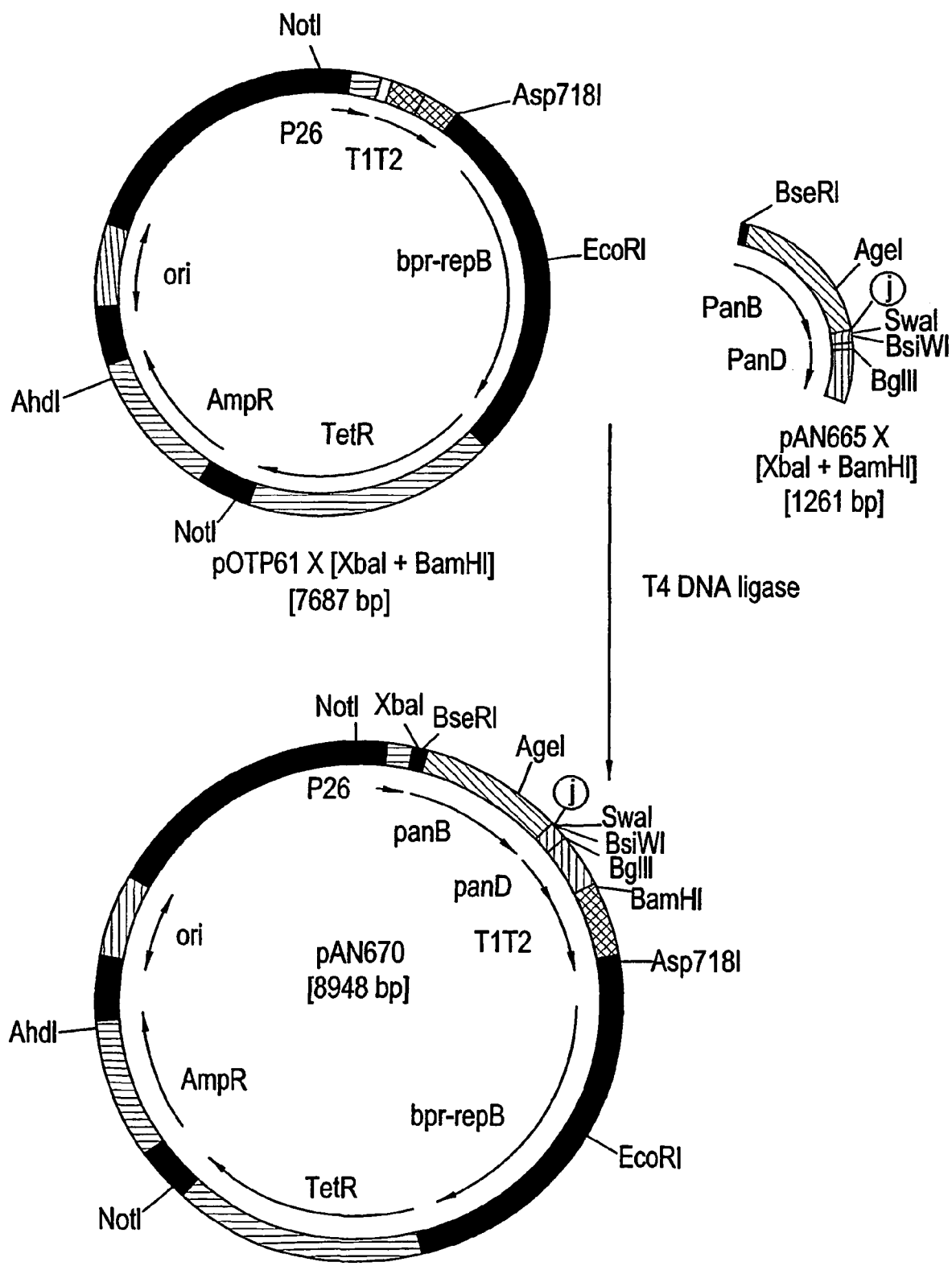
FIG. 4 is a schematic representation of the construction of the plasmid pAN670.

A third production strain, PA721B-39, was engineered to further include an amplifiable P$_{26}$ panBpanD cassette as follows. First, a single expression cassette was constructed that is capable of integrating both panB and panD at the bpr locus. Combining both genes into one expression cassette simplifies the resulting strain by eliminating an antibiotic resistance marker. The P$_{26}$ panBpanD expression cassette was constructed to include each of two different panD ribosome binding sites (the RBSs having previously been synthesized and tested in International Public. No. WO 01/21772 and U.S. Patent Application No. 60/262,995). The cassette further included the synthetic panB gene ribosome binding site (RBS1), but the design permits future alteration of the panB RBS by simple oligonucleotide cassette substitution. In the first step of construction, the panB gene was joined to the two panD gene cassettes as illustrated in FIG. 3 for the construction of pAN665. Next, the resulting panBpanD cassettes were transferred to *B. subtilis* expression vector pOTP61 as illustrated in FIG. 4. A summary of the essential features of each plasmid (pAN670 and pAN674) constructed is presented in Table 1.

TABLE 1

Plasmids containing various *B. subtilis* panBpanD gene expression cassettes.

| Plasmid | panD RBS | Vector | Host strain |
|---|---|---|---|
| pAN665 | Standard | pASK-1BA3 | E.coli |
| pAN670 | " | pOTP61 | B. subtilis |
| pAN669 | ND-C2 | pASK-1BA3 | E. coli |
| pAN674 | " | pOTP61 | B. subtilis |

These new plasmids combine production of extra PanB and PanD from a single vector and were predicted to produce increased levels of PanB relative to the panB expression vector (pAN636) present in PA668. The strategy to install the P26 panBpanD vectors in pantothenate production strains took advantage of genetic linkage between bpr and panE1. A derivative of PA824 was first constructed that is cured of the resident panD expression cassette by transforming the strain with chromosomal DNA isolated from PA930 panE1::cat) and selecting for resistance to chloramphenicol. The resulting transformants were screened for sensitivity to tetracycline, and two Tet-sensitive isolates named PA715 were saved. This strain is the host strain for testing the P26 panBpanD vectors (see below). In order to restore the P26 panE1 cassette in PA715, each vector was first transformed into a strain (PA328) that contains P26 panE1 but does not contain a cassette integrated at the bpr locus. PA328 does contain the P26 panBCD locus although it is not engineered for overproduction of α-KIV. Transformants of PA328 resistant to tetracycline were obtained using the appropriate NotI restriction fragments from the two vectors and the resulting strains were named PA710 and PA714.

The next step was to transfer the cassettes into PA715 so they could be evaluated in the PA824 strain background. This was accomplished by isolating chromosomal DNA from strains PA710 and PA714 and using each of the two DNAs separately to transform PA715, with selection for resistance to tetracycline. Tetracycline-resistant transformants were screened for sensitivity to chloramphenicol; this identifies the desired transformants that have also acquired the P26 panE1 gene from the donor DNA by linkage with the P26 panBpanD cassettes at the bpr locus. Chloramphenicol-sensitive isolates derived from transformations in which PA710 or PA714 chromosomal DNA was used as the donor were obtained. The isolates that produced the highest pantothenate titers in test tube culture assays were saved. These strains were named PA717 and PA721, respectively. Duplicate test tube cultures of the new strains, as well as PA824 and PA715, were grown in SVY+10 g/L aspartate at 43° C. for 48 hours and then assayed for pantothenate, HMBPA, and β-alanine. In addition, extracts from each of the strains were run on a SDS-PAGE gel. The results of the test tube culture assays are presented in Table 2.

TABLE 2

Production of pantothenate by strains PA717 and PA721 grown in SVY plus 10 g/l aspartate.

| Strain | panBD cassette | [pan] (g/L) | [HMBPA] (g/L) | [β-ala] (g/L) |
|---|---|---|---|---|
| PA824 | — | 4.9 | 0.94 | 2.5 |
| " | | 4.6 | 0.79 | 2.3 |
| PA715 | NONE | 1.7 | <0.1 | 0.5 |
| " | " | 1.7 | <0.1 | 0.4 |
| PA717-24 | pAN670 | 4.8 | 0.34 | 1.3 |
| " | " | 4.9 | 0.40 | 1.3 |
| PA721-35 | pAN674 | 5.7 | 0.50 | 1.4 |
| " | " | 5.3 | 0.40 | 1.3 |
| PA721-39 | pAN674 | 4.1 | 0.38 | 2.0 |
| " | " | 4.6 | 0.40 | 2.2 |

As expected, each of the new strains produced more pantothenate and β-alanine than PA715. Two of the strains (PA717-24 and PA721-39) produced about as much pantothenate as PA824 while PA721-35 produced more pantothenate than PA824. All three of the new strains produced less HMBPA than PA824. The protein gel analysis showed that the three new strains produce more PanB than any of the control strains.

Strains PA717-24, PA721-35, and PA721-39 were also evaluated in shake flask cultures in a soy flour based medium. As shown in Table 3, these strains with the amplifiable $P_{26}$ panBpanD cassette produced pantothenate and HMBPA at levels similar to the levels seen with PA668-2 and PA668-24 which both contain separate amplifiable $P_{26}$ panB and $P_{26}$ panD cassettes.

TABLE 3

Shake Flask Experiment 48 Hours

| Medium | Strain | HMBPA (g/l) | PAN (g/l) |
|---|---|---|---|
| Soy flour + Glucose | PA668-2 | 1.2 | 6.8 |
|  | PA668-24 | 1.6 | 5.2 |
|  | PA717-24 | 2.0 | 5.9 |
|  | PA721-35 | 2.6 | 7.0 |
|  | PA721-39 | 2.5 | 8.6 |
| Soy flour + Maltose | PA668-2 | 0.0 | 9.0 |
|  | PA668-24 | 0.4 | 10.4 |
|  | PA717-24 | 0.7 | 8.6 |
|  | PA721-35 | 1.0 | 9.2 |
|  | PA721-39 | 0.4 | 9.1 |

Conditions: 40 ml medium/200 ml baffled shake flask, 4X Bioshield covers, 300 rpm. 2.5% inoculum (1.0 ml).
Soy Medium: 20 g/l Cargill 200/20 soy flour, 8 g/l (NH4)2SO4, 5 g/l glutamate, 1x PSTE, 0.1 M phosphate pH 7.2 and 0.3 M MOPS pH 7.2. 60 g/l glucose or maltose w/10 mM Mg and 1.4 mM Ca.
Average of duplicate flasks.

In addition to producing pantothenate (as well as other panto-compounds depicted in FIG. 1 and described herein), it has been demonstrated that certain strains engineered for producing commercial quantities of desired panto-compound also produce a by-product identified as 3-(2-hydroxy-3-methyl-butyrylamino)-propionic acid (HMBPA) (also referred to herein as "β-alanine 2-(R)-hydroxyisolvalerate", "β-alanine 2-hydroxyisolvalerate", "β-alanyl-α-hydroxyisovalarate" and/or "fantothenate"). (The term "fantothenate" is also abbreviated as "fan" herein.)

HMBPA is the condensation product of [R]-α-hydroxyisovaleric acid (α-HIV) and α-alanine, catalyzed by the PanC enzyme. α-HIV is generated by reduction of α-KIV, a reaction that is catalyzed by the α-keto reductases PanE (e.g., PanE1 and/or PanE2) and/or IlvC. Thus it has been proposed that there exist at least two pathways in microorganisms that compete for α-KIV, the substrate for the biosynthetic enzyme PanB, namely the pantothenate biosynthetic pathway and the HMBPA biosynthetic pathway. (A third and fourth pathway competing for α-KIV are those resulting in the production of valine or leucine from α-KIV, see e.g., FIG. 1). At least the pantothenate biosynthetic pathway and the HMBPA biosynthetic pathway further produce competitive substrates for the enzyme PanC, namely α-HIV and pantoate. Production of HMBPA can have significant effects on pantothenate production. For example, the HMBPA pathway can compete with the pantothenate pathway for precursors (α-KIV and β-alanine) and for some of the enzymes (PanC, PanD, PanE1, and/or IlvC). In addition, because the structure of HMBPA is similar to that of pantothenate, it may have the undesirable property of negatively regulating one or more steps in the pantothenate pathway. Based on the identification of HMBPA, U.S. Provisional Patent Application Ser. No. 60/262,995 teaches that production of pantothenate can be improved or optimized by any means which favor use of substrates (α-KIV and β-alanine) and/or enzymes (PanC, PanD, PanE1, and/or IlvC) in pantothenate biosynthetic processes as compared to HMBPA biosynthetic processes.

Example II

Increasing Pantothenate Production by Increasing Serine Availability

At least one method for optimizing pantothenate production involves regulating the availability of serine in the microorganism cultures. In particular, it can be demonstrated that increasing the availability of serine leads to increased pantothenate production (e.g. relative to HMBPA production), whereas decreasing the availability of serine leads to decreased pantothenate production relative to HMBPA production. This method is based on the understanding that the compound, methylenetetrahydrofolate (MTF), which is derived from serine, donates a hydroxymethyl group to α-KIV during the pantothenate biosynthetic reaction to yield ketopantoate (see e.g., FIGS. 1 and 2). Thus, regulating serine levels is one means of effectively regulating ketopantoate levels and, in turn, regulating pantoate and/or pantothenate production in appropriately engineered microorganisms. To demonstrate this regulation, PA824 was grown in test tube cultures of SVY glucose plus 5 g/L β-alanine and ±5 g/L serine for 48 hours and 43° C.

TABLE 4

Production of pantothenate and HMBPA by PA824 with and without the addition of serine

| serine added at 5 g/L | $OD_{600}$ | [pan] g/L | [HMBPA] g/L |
|---|---|---|---|
| – | 16.3 | 4.9 | 0.84 |
| – | 14.0 | 4.5 | 0.80 |
| + | 13.1 | 6.4 | 0.56 |
| + | 12.9 | 6.0 | 0.62 |

As demonstrated by the data presented in Table 4, addition of serine increases the level of production of pantothenate (while conversely decreasing HMBPA production).

Example III

Engineering Bacterial Cells with Increased Amounts of Serine Hydroxylmethyl Transferase, the glyA Gene Product As an alternative to feeding serine, another method of increasing serine levels and/or serine utilization levels (and accordingly, methylenetetrahydrofolate levels) in order to regulate pantothenate production levels is to increase synthesis or the activity of 3-phosphoglycerate dehydrogenase or of serine hydroxymethyl transferase (the serA and glyA gene products, respectively), thereby increasing serine and methylenetetrahydrofolate biosynthesis in appropriately engineered microorganisms.

Expression of the glyA gene was increased by transforming B. subtilis cells with an expression cassette containing the B. subtilis glyA gene cloned downstream of a strong, constitutive promoter. To construct the expression cassette the primers RY417 and RY418 depicted in Table 5 were used to amplify the glyA gene by PCR from chromosomal DNA isolated from B. subtilis PY79.

TABLE 5

Primers used in the amplification of B. subtilis glyA and serA

| | | |
|---|---|---|
| RY405 | CCCTCTAGAGGAGGAGAAAACATGTTTCGAG TATTGGTCTCAGACAAAATG | SEQ ID NO:20 |
| RY406 | CCCGGATCCAATTATGGCAGATCAATGAGCT TCACAGACACAA | SEQ ID NO:21 |
| RY417 | GGATCTAGAGGAGGTGTAAACATGAAACATT TACCTGCGCAAGACGAA | SEQ ID NO:22 |
| RY418 | CGGGGATCCCCCATCAACAATTACACACTTC TATTGATTCTAC | SEQ ID NO:23 |

Figure 5:
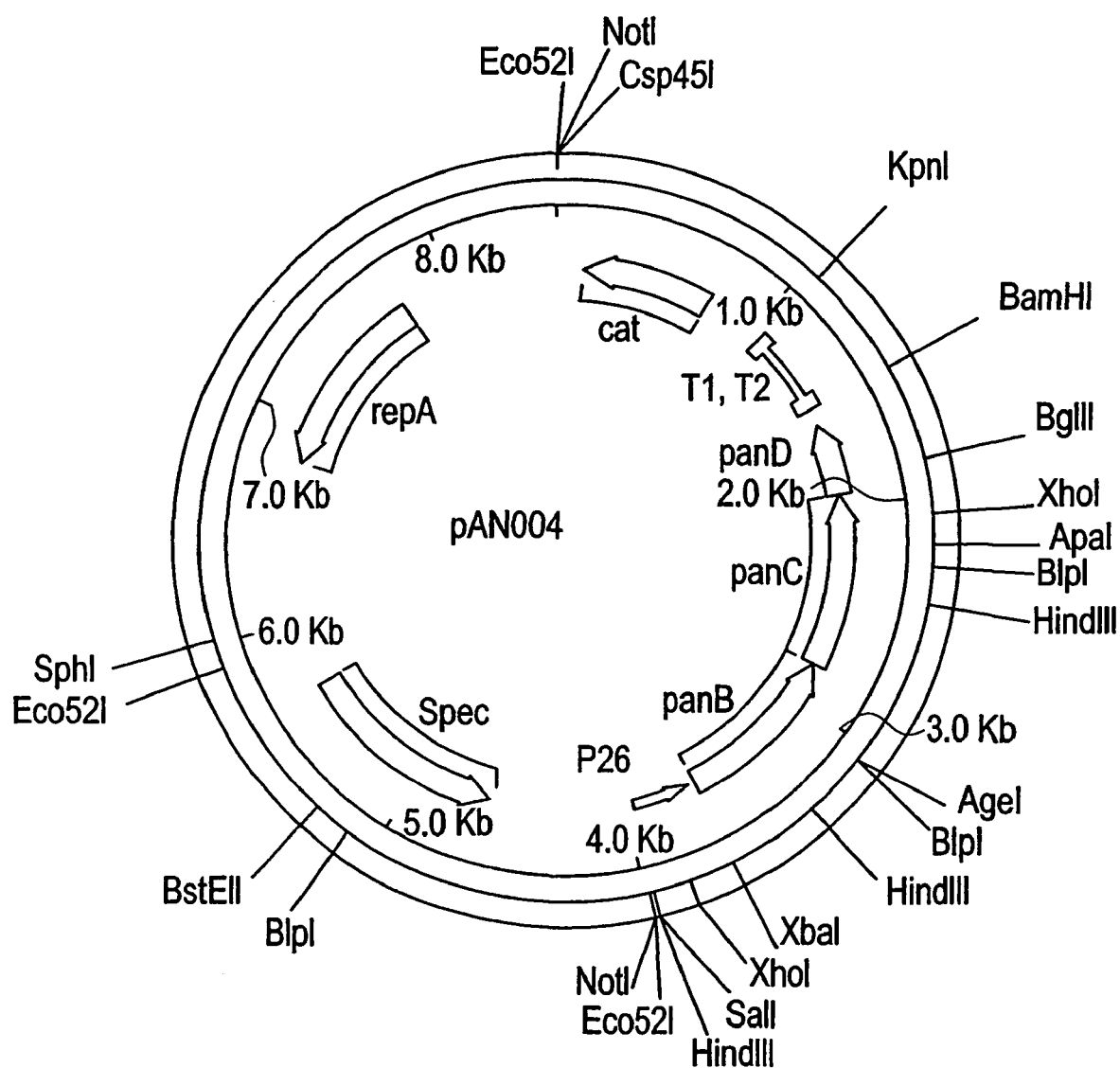
FIG. 5 is a schematic representation of the plasmid pAN004.
Figure 6:
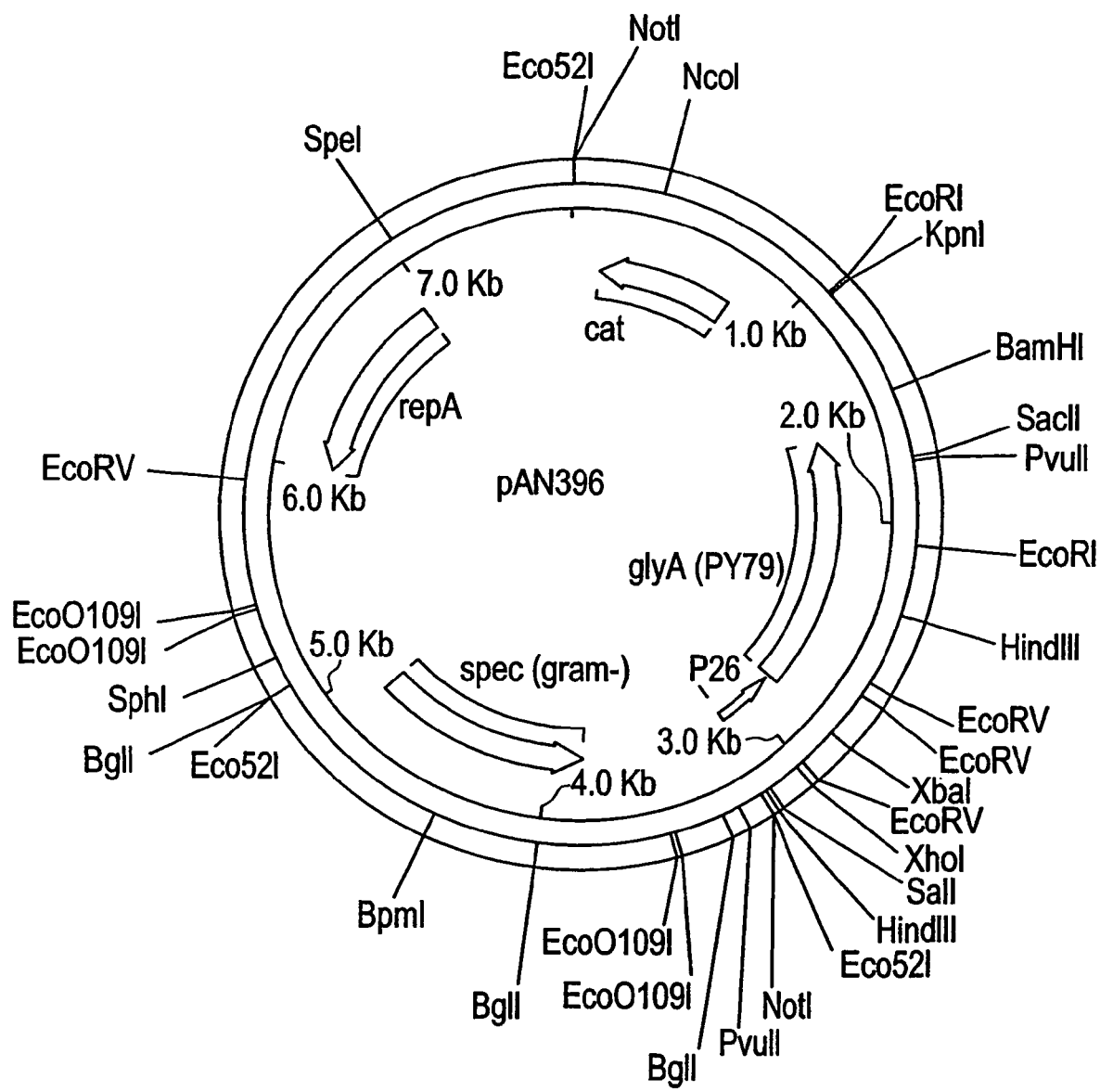
FIG. 6 is a schematic representation of the plasmid pAN396.

RY417 contains the RBS2 synthetic ribosome binding site just downstream from an XbaI site. The amplified DNA was then cut with XbaI and BamHI and cloned between the XbaI and BamHI sites in vector pAN004 (FIG. 5) to yield plasmid pAN396 (FIG. 6; SEQ ID NO:24). The pAN004 vector contains the phage SP01 $P_{26}$ promoter immediately upstream of the XbaI cloning site to drive expression of the cloned glyA gene. Just downstream of the expression cassette, pAN396 contains a cat gene that functions in *B. subtilis*. To transform *B. subtilis*, the NotI DNA fragment containing the $P_{26}$ glyA cassette and cat gene was isolated from pAN396, self-ligated, and transformed into competent cells of *B. subtilis* PY79. Several chloramphenicol resistant transformants were selected and named PA1007 and PA1008. Chromosomal DNA was isolated from each of these strains and used to transform competent cells of PA721B-39 and PA824 to yield strains PA1011 and PA1014, respectively. SDS polyacrylamide gel electrophoresis of cell extracts of selected isolates of PA1011 and PA1014 confirmed that these strains contained increased amounts of the glyA gene product as compared to their parent strains PA721B-39 (described in Example I) and PA824 (described in International Public. No. WO 01/21772). To test the effect of increasing glyA expression on pantothenate production, PA1011 and PA1014 were grown in test tube cultures of SVY glucose plus 5 g/L β-alanine at 43° C. for 48 hours. As shown by the data presented in Table 6, PA 1014 produced more pantothenate (4.5 g/L) than its parent strain PA824 (3.2 g/L). Similarly, PA1011 produced on average more pantothenate (4.35 g/L) than its parent strain PA721B-39 (4.05 g/L).

TABLE 6

Production of pantothenate and HMBPA by PA1011 and PA1014 compared to PA721B-39 and PA824.

| Strain | $OD_{600}$ | Pantothenate g/L | HMBPA g/L |
|---|---|---|---|
| PA1014 #1 | 14 | 4.5 | 0.27 |
| PA1014 #2 | 15 | 4.5 | 0.31 |
| PA824 | 16 | 3.1 | 0.31 |
| PA824 | 15 | 3.3 | 0.28 |
| PA1011 #1 | 17 | 4.5 | 0.24 |
| PA1011 #2 | 12 | 4.2 | 0.27 |
| PA721B-39 | 18 | 4.0 | 0.22 |
| PA721B-39 | 16 | 4.1 | 0.25 |

Example IV

Figure 7:
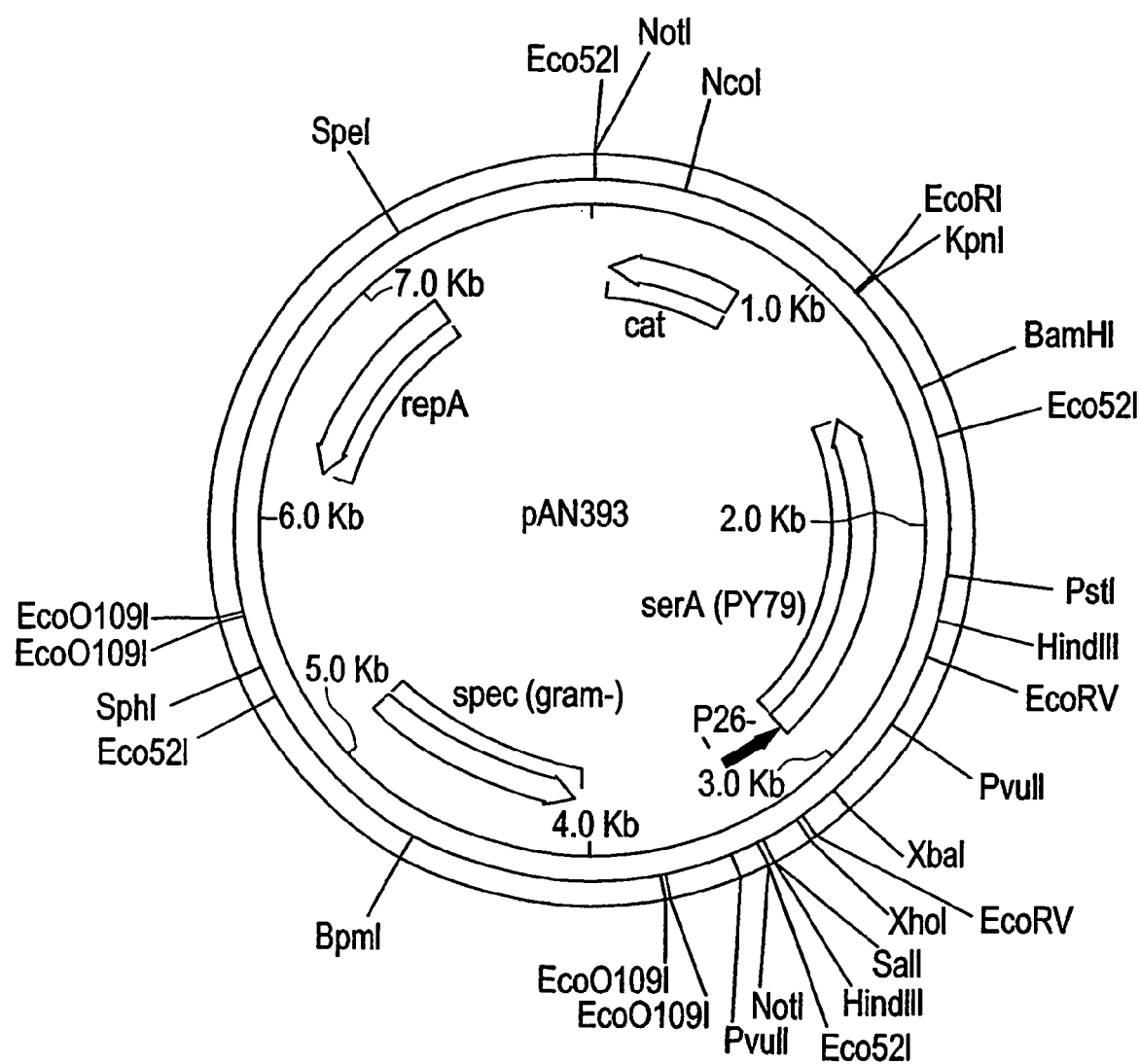
FIG. 7 is a schematic representation of the plasmid pAN393.

Engineering Bacterial Cells with Increased Amounts of 3-phosphoglycerate Dehydrogenase, the serA Gene Product The product of the serA gene, 3-phosphoglycerate dehydrogenase, is the first committed enzyme in the pathway to serine biosynthesis (see FIG. 2). Since serine is one of the substrates for the synthesis of MTF, we engineered the overexpression of the serA gene to increase serine levels in the cell. In a manner similar to that described above for the glyA gene in Example III, expression of the serA gene was increased by transforming *B. subtilis* cells with an expression cassette containing the *B. subtilis* serA gene cloned downstream of a strong, constitutive promoter. To construct the expression cassette the primers RY405 and RY406 depicted in Table 5 were used to amplify the serA gene by PCR from chromosomal DNA isolated from *B. subtilis* PY79. The amplified DNA was then cut with XbaI and BamHI and cloned between the XbaI and BamHI sites in vector pAN004 (FIG. 5) to yield plasmid pAN393 (FIG. 7; SEQ ID NO:25). To transform *B. subtilis*, the NotI DNA fragment containing the $P_{26}$ serA cassette and cat gene was isolated from pAN393, self-ligated, and transformed into competent cells of *B. subtilis* PY79. Several chloramphenicol resistant transformants were selected and named PA1004 and PA1005. Chromosomal DNA was isolated from each of these strains and used to transform competent cells of PA721B-39 and PA824 to yield strains PA1010 and PA1013, respectively. SDS polyacrylamide gel electrophoresis of cell extracts of selected isolates of PA1010 and PA1013 confirmed that these strains contained increased amounts of the serA gene product as compared to their parent strains PA721B-39 and PA824.

To test the effect of increasing serA expression on pantothenate production, PA1010 and PA1013 were grown in test tube cultures of SVY glucose plus 5 g/L β-alanine at 43° C. for 48 hours. As shown by the data presented in Table 7, PA1010 produced on average more pantothenate (4.7 g/L) than its parent strain PA721B-39 (4.1 g/L). Similarly, PA1013 produced on average more pantothenate (4.1 g/L) than its parent strain PA824 (3.1 g/L).

TABLE 7

Production of pantothenate and HMBPA by PA1010 and PA1013 compared to PA721B-39 and PA824.

| Strain | $OD_{600}$ | Pantothenate g/L | HMBPA g/L |
|---|---|---|---|
| PA1010 #3 | 16 | 4.8 | 0.23 |
| PA1010 #5 | 15 | 4.5 | 0.26 |
| PA1010 #6 | 22 | 4.7 | 0.24 |
| PA721B-39 | 18 | 4.0 | 0.22 |
| PA721B-39 | 16 | 4.1 | 0.25 |
| PA1013 #2 | 14 | 3.3 | 0.25 |
| PA1013 #4 | 14 | 4.2 | 0.28 |
| PA1013 #5 | 16 | 5.5 | 0.37 |
| PA1013 #8 | 13 | 3.6 | 0.24 |
| PA824 | 17 | 3.0 | 0.27 |
| PA824 | 16 | 3.1 | 0.29 |

Example V

Shake Flask and Fermentor Experiments with Strains with Increased Expression of serA and glyA Based on performance in test tubes, two strains with an amplifiable serA cassette and two strains with an amplifiable glyA cassette were selected, one each from two parents, PA824 and PA721B-39. The four strains were grown beside the parents in shake flasks (Table 8). In Soy flour MOPS Glucose (SMG) medium, all of the 4 strains produced more pantothenate than their parent strains. In Soy flour MOPS Maltose (SMM) medium one out of the four strains appeared superior to the parent strain.

The serA overexpressing strain and the glyA overexpressing strain from each parent were run simultaneously in 10-liter Chemap bench fermentors. The glyA overexpressing strain derived from PA824, PA1014-3, that had given the highest pantothenate titer in SMM, also performed the best in fermentors (Table 9). Strain PA1014-3 produced 71 g/l pantothenate in 36 hours in the culture supernatant and 86 g/l pantothenate in 48 hours in the culture supernatant compared to the parent PA824 which produced 41 g/l and 46 g/l pantothenate, respectively. The serA strain, PA1012-4, also produced significantly more pantothenate than the PA824 control in the culture supernatant, 52 g/l and 60 g/l at 36 and 48 hours, respectively. These results clearly demonstrate the effectiveness of increasing both glyA and serA.

The serA overexpressing and glad overexpressing derivatives of PA721B-39 were clearly improved over their parent strain as well. Both produced about 80 g/l pantothenate (82 g/l and 79 g/l, respectively) in the culture supernatants in 48 hours. The effect of the increased PanB levels in the PA721B-39 derivatives versus the PA824 derivatives manifests itself in the reduction of HMBPA. PA721B-39 and its derivatives produce less HMBPA after 48 hours than PA824 or even PA668-24. Increasing GlyA also appears to lower the flow of carbon to HMBPA.

TABLE 8

Shake flask evaluation of pantothenate production strains overexpressing ser A or gly A.

| Carbon source | Strain | Added cassette | HMBPA (g/l) | Pantothenate (g/l) |
|---|---|---|---|---|
| Glucose | PA824 | | 3.5 | 4.0 |
| | PA1012-4 | serA | 3.0 | 4.6 |
| | PA1014-3 | gly A | 2.5 | 4.7 |
| | PA721B-39 | | 0.9 | 5.0 |
| | PA1010-6 | serA | 1.9 | 9.6 |
| | PA1011-2 | gly A | 1.7 | 10.0 |
| Maltose | PA824 | | 1.2 | 10.4 |
| | PA1012-4 | serA | 0.8 | 9.8 |
| | PA1014-3 | gly A | 1.1 | 16.1 |
| | PA721B-39 | | 0.6 | 11.6 |
| | PA1010-6 | serA | 0.5 | 10.2 |
| | PA1011-2 | gly A | 0 | 10.3 |

All data are the average of duplicate shake flasks after 48 hours.
Conditions: 40 ml medium/200 ml baffled shake flask, 4X Bioshield covers, 300 rpm, 2.5% inoculum and 43° C.
Medium: 20 g/l Cargill 200/20 soy flour, 1 x PSTE, 8 g/l (NH4)2SO4 and 5 g/l glutamate.
Buffer: 0.1 M phosphate pH 7.2 and 0.3 M MOPS pH 7.2.
Carbon Source (Sterilized separately as 20 x stock): 60 g/l glucose or maltose w/ 10 mM Mg and 1.4 mM Ca.

TABLE 9

10 liter fermentor evaluations of pantothenate production strains overexpressing serA or glyA.

| | | | | HMBPA (g/l) | | Pantothenate (g/l) | |
|---|---|---|---|---|---|---|---|
| run | Strain | Parent | Added cassette | 36 hrs | 48 hrs | 36 hrs | 48 hrs |
| P285 | PA824 | | | 18 | 25 | 41 | 46 |
| P284 | PA1012-4 | PA824 | serA | 20 | 21 | 52 | 60 |
| P286 | PA1014-3 | PA824 | glyA | 14 | 16 | 71 | 86 |
| P259 | PA721B-39 | | | 4 | 5 | 34 | 42 |
| P287 | PA1010-6 | PA721B-39 | serA | 4 | 5 | 65 | 82 |
| P289 | PA1011-2 | PA721B-39 | glyA | 2 | 3 | 56 | 79 |
| P275 | PA668-24 | PA824 | | 3 | 9 | 55 | 72 |

The medium used is PFM-222. It is the same as medium PFM-155 described in U.S. Ser. No. 60/262,995 (filed Jan. 19, 2001) except for the following changes: (1) In the Batch Material: There is no Amberex 1003. Cargill 200/20 (soy flour) 40 g/L has been changed to Cargill 20–80 (soy grits) 50 g/L, $MgSO_4 \cdot 7H_2O$ is replaced with $MgCl_2 \cdot 7H_2O$, 1 g/L, and SM-1000X is replaced with PSTE-1000X (PSTE-1000X = $MnCl_2 \cdot 4H_2O$, 2.0 g/L; $ZnSO_4 \cdot 7H_2O$, 1.5 g/L; $CoCl_2 \cdot 6H_2O$, 2.0 g/L; $CuSO_4 \cdot 5H_2O$, 0.25 g/l; $Na_2MoO_4 \cdot 2H_2O$, 0.75 g/L). In the Feed Material: SM-1000X is replaced with PSTE-1000X Increasing pantothenate production can also be achieved by combining overexpression of serA and glyA in a single strain, and/or by introducing a mutation that leads to feedback resistant serA or glyA, or both.

Equivalents Those skilled in the art will recognize, or be able to ascertain using no more than routine experimentation, many equivalents to the specific embodiments of the invention described herein. Such equivalents are intended to be encompassed by the following claims.

What is claimed:

1. A process for the enhanced production of pantothenate, comprising culturing a microorganism having a methylene-tetrahydrofolate (MTF) biosynthetic enzyme encoded by a *Bacillus* serA and/or a *Bacillus* glyA gene overexpressed, under conditions such that pantothenate production is enhanced.

2. A process for the enhanced production of pantothenate, comprising culturing a microorganism having (i) an increased level of a *Bacillus* pantothenate biosynthetic enzyme gene product selected from the group consisting of: ketopantoate hydroxymethyltransferase, ketopantoate reductase, pantothenate synthetase, and aspartate-α-decarboxylase, and (ii) an overexpressed methylenetetrahydrofolate (MTF) biosynthetic enzyme encoded by a *Bacillus* serA and/or a *Bacillus* glyA gene, under conditions such that pantothenate production is enhanced.

3. The process of claim 2, wherein said microorganism has an increased level of at least two pantothenate biosynthetic enzyme gene products.

4. The process of claim 2, wherein said microorganism has an increased level of at least three pantothenate biosynthetic enzyme gene products.

5. The process of claim 2, wherein said microorganism has an increased level of at least four pantothenate biosynthetic enzyme gene products.

6. The process of claim 5, wherein said microorganism has an increased level of the pantothenate biosynthetic enzyme gene product ketopantoate hydroxymethyltransferase, ketopantoate reductase, pantothenate synthetase and aspartate-α-decarboxylase.

7. The process of any one of claim 1 or 2, wherein said microorganism further has an increased level of an isoleucine-valine (ilv) biosynthetic enzyme gene product selected from the group consisting of: acetohydroxyacid acid synthetase, acetohydroxyacid isomeroreductase, and dihydroxyacid dehydratase.

8. The process of claim 7, wherein said microorganism has increased levels of at least two isoleucine-valine (ilv) biosynthetic enzyme gene products.

9. The process of claim 7, wherein said microorganism has increased levels of at least three isoleucine-valine (ilv) biosynthetic enzyme gene products.

10. The process of claim 9, wherein said microorganism has increased levels of the isoleucine-valine (ilv) biosynthetic enzyme gene product acetohydroxyacid acid synthetase, acetohydroxyacid isomeroreductase, and dihydroxyacid dehydratase.

11. The process of claim 2, wherein the microorganism has an overexpressed glyA gene.

12. The process of claim 2, wherein the microorganism has an overexpressed serA gene.

13. The process of claim 2, wherein the microorganism has an overexpressed glyA gene and an overexpressed serA gene.

14. The process of any one of claims 1 or 2, wherein pantothenate production is further enhanced by decreasing pantothenate kinase activity.

15. The process of claim 1, wherein said microorganism is cultured under conditions of excess serine.

16. The process of claim 15, wherein said microorganism is cultured in the presence of greater than 2.5 g/L of serine.

17. The process of claim 15, wherein said microorganism is cultured in the presence of greater than 5 g/L of serine.

18. A process for the enhanced production of pantothenate, comprising culturing a microorganism overexpressing a *Bacillus* panB gene and having at least one methylenetetrahydrofolate (MTF) biosynthetic enzyme encoded by a gene selected from the group consisting of *Bacillus* serA, *Bacillus* serB, *Bacillus* serC, *Bacillus* mtrA, *Bacillus* sul, *Bacillus* fol, *Bacillus* pab, *Bacillus* gcv, and/or *Bacillus* glyA overexpressed, under conditions such that pantothenate production is enhanced.

19. A process for the enhanced production of pantothenate, comprising culturing a microorganism overexpressing a *Bacillus* panB gene and having at least one methylenetetrahydrofolate (MTF) biosynthetic enzyme encoded by a gene selected from the group consisting of *Bacillus* serA, *Bacillus* mtrA, *Bacillus* sul, *Bacillus* fol, *Bacillus* *Bacillus* pab, *Bacillus* gcv, and/or *Bacillus* glyA overexpressed, under conditions such that pantothenate production is enhanced.

20. A process for the enhanced production of pantothenate, comprising culturing a microorganism having
(i) an increased level of a *Bacillus* pantothenate biosynthetic enzyme gene product selected from the group consisting of: ketopantoate hydroxymethyltransferase, ketopantoate reductase, pantothenate synthetase, and aspartate-α-decarboxylase, and
(ii) an overexpressed methylenetetrahydrofolate (MTF) biosynthetic enzyme encoded by a gene selected from the group consisting of: *Bacillus* serA, *Bacillus* mtrA, *Bacillus* sul, *Bacillus* fol, *Bacillus* pab, *Bacillus* gcv, and/or *Bacillus* glyA, under conditions such that pantothenate production is enhanced.

21. The process of claim 20, wherein said microorganism has an increased level of at least two pantothenate biosynthetic enzyme gene products.

22. The process of claim 20, wherein said microorganism has an increased level of at least three pantothenate biosynthetic enzyme gene products.

23. The process of claim 20, wherein said microorganism has an increased level of at least four pantothenate biosynthetic enzyme gene products.

24. The process of claim 23, wherein said microorganism has an increased level of the pantothenate biosynthetic enzyme gene product ketopantoate hydroxymethyltransferase, ketopantoate reductase, pantothenate synthetase and aspartate-α-decarboxylase.

25. The process of any one of claims 18, 19, or 20, wherein said microorganism further has an increased level of an isoleucine-valine (ilv) biosynthetic enzyme gene product selected from the group consisting of: acetohydroxyacid acid synthetase, acetohydroxyacid isomeroreductase, and dihydroxyacid dehydratase.

26. The process of claim 25, wherein said microorganism has increased levels of at least two isoleucine-valine (ilv) biosynthetic enzyme gene products.

27. The process of claim 25, wherein said microorganism has increased levels of at least three isoleucine-valine (ilv) biosynthetic enzyme gene products.

28. The process of claim 27, wherein said microorganism has increased levels of the isoleucine-valine (ilv) biosynthetic enzyme gene product acetohydroxyacid acid synthetase, acetohydroxyacid isomeroreductase, and dihydroxyacid dehydratase.

29. The process of any one of claims 18, 19, or 20, wherein the microorganism has a serA or glyA gene overexpressed.

30. The process of claim 29, wherein the microorganism has an overexpressed glyA gene.

31. The process of claim 29, wherein the microorganism has an overexpressed serA gene.

32. The process of claim 29, wherein the microorganism has an overexpressed glyA gene and an overexpressed serA gene.

33. The process of any one of claims 18, 19, or 20, wherein pantothenate production is further enhanced by decreasing pantothenate kinase activity.

34. The process of any one of claims 18, 19, or 20, wherein said microorganism is cultured under conditions of excess serine.

* * * * *

UNITED STATES PATENT AND TRADEMARK OFFICE
CERTIFICATE OF CORRECTION

PATENT NO. : 7,244,593 B2
APPLICATION NO. : 10/466641
DATED : July 17, 2007
INVENTOR(S) : R. Rogers Yocum et al.

It is certified that error appears in the above-identified patent and that said Letters Patent is hereby corrected as shown below:

In Claim 1, at column 53, line 65, "serA" and "glyA" should be --*serA*-- and --*glyA*--;

In Claim 2, at column 55, line 2, "serA" should be --*serA*--;

In Claim 2, at column 55, line 3, "glyA" should be --*glyA*--;

In Claim 11, at column 55, line 38, "glyA" should be --*glyA*--;

In Claim 12, at column 55, line 40, "serA" should be --*serA*--;

In Claim 13, at column 55, line 42, "glyA" and "serA" should be --*glyA*-- and --*serA*--;

In Claim 18, at column 55, line 57, "serA" should be --*serA*--;

In Claim 18, at column 55, line 58, "serB", "serC" and "mtrA" should be --*serB*--, --*serC*-- and --*mtrA*--;

In Claim 18, at column 55, line 59, "glyA" should be --*glyA*--;

In Claim 19, at column 55, line 64, "panB" should be --*panB*--;

In Claim 19, at column 55, line 66, "serA" should be --*serA*--;

In Claim 19, at column 55, line 67, "mtrA" should be --*mtrA*--;

In Claim 19, at column 55, line 67, the fifth "Bacillus" should be deleted;

In Claim 19, at column 56, line 1, "glyA" should be --*glyA*--;

In Claim 20, at column 56, line 13, "serA" and "mtrA" should be --*serA*-- and --*mtrA*--;

In Claim 20, at column 56, line 14, "sul", "fol", "pab", "gcv" should be --*sul*--, --*fol*--, --*pab*-- and --*gcv*--;

In Claim 20, at column 56, line 15, "glyA" should be --*glyA*--;

In Claim 29, at column 56, line 51, "serA" and "glyA" should be --*serA*-- and --*glyA*--;

In Claim 30, at column 56, line 54, "glyA" should be --*glyA*--;

UNITED STATES PATENT AND TRADEMARK OFFICE
CERTIFICATE OF CORRECTION

PATENT NO. : 7,244,593 B2
APPLICATION NO. : 10/466641
DATED : July 17, 2007
INVENTOR(S) : R. Rogers Yocum et al.

It is certified that error appears in the above-identified patent and that said Letters Patent is hereby corrected as shown below:

In Claim 31, at column 56, line 56, "serA" should be --*serA*--;

In Claim 32, at column 56, line 58, "glyA" and "serA" should be --*glyA*-- and --*serA*--.

Signed and Sealed this

Sixth Day of November, 2007

JON W. DUDAS
*Director of the United States Patent and Trademark Office*